United States Patent [19]
Graham et al.

[11] Patent Number: 5,965,578
[45] Date of Patent: Oct. 12, 1999

[54] INHIBITORS OF FARNESYL-PROTEIN TRANSFERASE

[75] Inventors: Samuel L. Graham, Schwenksville; Theresa M. Williams; John S. Wai, both of Harleysville, all of Pa.

[73] Assignee: Merck & Co., Inc., Rahway, N.J.

[21] Appl. No.: 08/823,934

[22] Filed: Mar. 25, 1997

Related U.S. Application Data

[60] Provisional application No. 60/014,793, Apr. 3, 1996.
[51] Int. Cl.$^6$ .................. A61K 31/445; C07D 401/06
[52] U.S. Cl. .................. 514/326; 514/318; 546/184; 546/208; 546/210
[58] Field of Search .................. 514/277, 318, 514/326; 540/485; 546/184, 208, 210

[56] References Cited

U.S. PATENT DOCUMENTS

| | | | |
|---|---|---|---|
| 5,159,083 | 10/1992 | Thurkauf et al. | 548/337 |
| 5,576,313 | 11/1996 | Fisher et al. | 514/211 |

FOREIGN PATENT DOCUMENTS

| | | |
|---|---|---|
| 0 332 295 | 9/1989 | European Pat. Off. |
| 0 675 112 A1 | 10/1995 | European Pat. Off. |
| S48-28679 | 10/1974 | Japan . |
| WO 96/06609 | 3/1996 | WIPO . |
| WO 96/30343 | 10/1996 | WIPO . |
| WO 96/31501 | 10/1996 | WIPO . |
| WO 96/37204 | 11/1996 | WIPO . |

OTHER PUBLICATIONS

Exp. Opin. Ther. Patents, vol. 5(12), pp. 1269–1271 (1995), by S. L. Graham.

Exp. Opin. Ther. Patents, vol. 6(12) (1996), pp. 1295–1304, by S. L. Graham, et al.

J. of Biol. Chem., vol. 268, No. 11, pp. 7617–7620 (1993), by J. B. Gibbs, et al.

J. of Biol. Chem., vol. 269, No. 44, pp. 27706–27714 (1994), by G. L. James, et al.

J. of Biol. Chem., vol. 270, No. 11, pp. 6221–6226 (1995), by G. L. James, et al.

Science, vol. 260, pp. 1934–1937 (1993), by N. E. Kohl, et al.

Proc. Natl. Acad. Sci. USA, vol. 91, pp. 9141–9145 (1994), by N. E. Kohl, et al.

Nature Medicine, vol. 1, No. 8, pp. 792–797 (1995), by N. E. Kohl, et al.

Cancer Research, vol. 55, pp. 5302–5309 (1995), by L. Sepp–Lorenzino, et al.

Kihara et al., "Preparation of 1-(thio)carbamoyl-and 1-alkoxycarbonylimidazoles for Improvement of Brain Function," Chemical Abstracts, vol. 112, No. 11, p. 753, (1990).

*Primary Examiner*—Amelia Owens
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

20 Claims, No Drawings

INHIBITORS OF FARNESYL-PROTEIN TRANSFERASE

This Application if a provision of Ser. No. 60/014,793 filed Apr. 3, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994) and induces regression of mammary and salivary carcinomas in ras transgenic mice (N. E. Kohl et al., *Nature Medicine,* 1:792–797 (1995).

Indirect inhibition of farnesyl-protein transferase in vivo has been demonstrated with lovastatin (Merck & Co., Rahway, N.J.) and compactin (Hancock et al., *ibid*; Casey et al., *ibid*; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell,* 62:81–88 (1990); Schaber et al., *J. Biol. Chem.,* 265:14701–14704 (1990); Schafer et al., *Science,* 249:1133–1139 (1990); Manne et al., *Proc. Natl. Acad. Sci USA,* 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., *ibid*; Reiss et. al., *ibid*; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science,* 260:1934–1937 (1993); Graham, et al., *J. Med. Chem.,* 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP.H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic piperidinone-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae A, B and C:

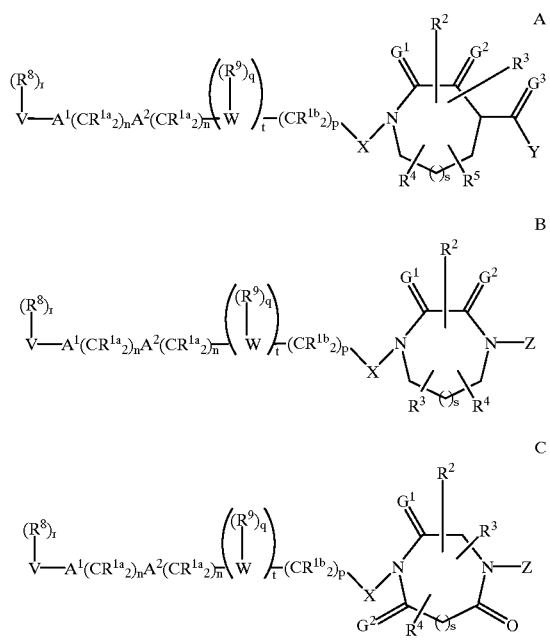

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

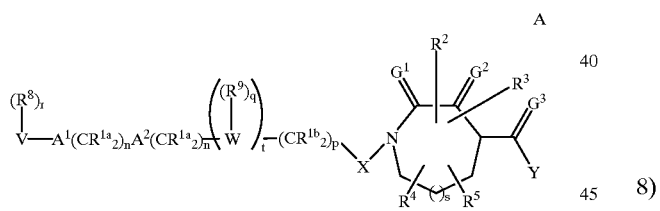

wherein:
$R^{1a}$ and $R^{1b}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $N_3$, —$N(R^{10})_2$, or $R^{11}OC(O)NR^{10}$—, and
  c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $N_3$, —$N(R^{10})_2$, and $R^{11}OC(O)$—$NR^{10}$—;
$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

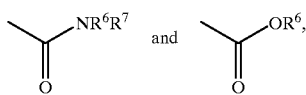

wherein the substituted group is substituted with one or more of:

1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
   f) aryl or heteroaryl,
   g) perfluoro-$C_{1-4}$ alkyl,
   h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$,
5) —$NR^6R^7$,
6) 
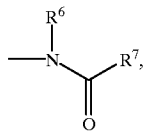
7)
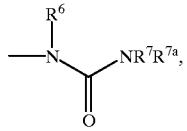
8)
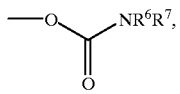
9)
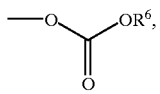
10)
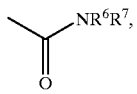
11) —$SO_2$—$NR^6R^7$, 12) 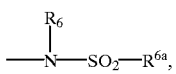

13) 

14) 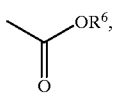

15) $N_3$,

16) F, or 17) perfluoro-$C_{1-4}$-alkyl; or $R^2$ and $R^3$ are attached to the same C atom and are combined to form —$(CH_2)_u$— wherein one of the carbon atoms is optionally replaced by a moiety selected from: O, $S(O)_m$, —NC(O)—, and —N($COR^{10}$)—;

$R^4$ and $R^5$ are independently selected from H and $CH_3$; and any two of $R^2$, $R^3$, $R^4$ and $R^5$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl and heteroarylsulfonyl, unsubstituted or substituted with:

a) $C_{1-4}$ alkoxy, b) aryl or heterocycle, c) halogen, d) HO, e) 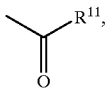

f) —$SO_2R^{11}$, or g) $N(R^{10})_2$; or $R^6$ and $R^7$ may be joined in a ring;

$R^7$ and $R^{7a}$ may be joined in a ring;

$R^{6a}$ is selected from: $C_{1-4}$ alkyl, $C_{3-6}$ cycloalkyl, heterocycle and aryl, unsubstituted or substituted with:

a) $C_{1-4}$ alkoxy, b) aryl or heterocycle, c) halogen, d) HO, e) 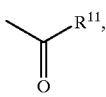

f) —$SO_2R^{11}$, or g) $N(R^{10})_2$;

$R^8$ is independently selected from:

a) hydrogen, b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—C($NR^{10}$)—, CN, $NO_2$, $R^{10}C(O)$—, $N_3$, —$N(R^{10})_2$, or $R^{11}OC(O)NR^{10}$—, and c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—C($NR^{10}$)—, CN, $R^{10}C(O)$—, $N_3$, —$N(R^{10})_2$, or $R^{10}OC(O)NH$—;

$R^9$ is selected from:

a) hydrogen, b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R_{10})_2NC(O)$—, $R^{10}_2N$—C($NR^{10}$)—, CN, $NO_2$, $R^{10}C(O)$—, $N_3$, —$N(R^{10})_2$, or $R^{11}OC(O)NR^{10}$—, and c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—C($NR^{10}$)—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —$C(O)NR^{10}$—, —$NR^{10}C(O)$—, O, —$N(R^{10})$—, —$S(O)_2N(R^{10})$—, —$N(R^{10})S(O)_2$— and $S(O)_m$;

$G^1$ and $G^2$ are independently oxygen or absent, provided that at least one of $G^1$ and $G^2$ is oxygen;

$G^3$ is oxygen or $H_2$;

V is selected from:

a) hydrogen, b) heterocycle, c) aryl, d) $C_1$–$C_{20}$ alkyl wherein from 0 to 4 carbon atoms are replaced with a heteroatom selected from O, S, and N, and e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is a bond, —$CH_2$—, —C(=O)—, or —S(=O)$_m$—;

Y is unsubstituted or substituted aryl or unsubstituted or substituted heterocycle, wherein the substituted aryl or substituted heterocycle is substituted with one or more of:

1) $C_{1-4}$ alkyl, unsubstituted or substituted with:

a) $C_{1-4}$ alkoxy, b) $NR^6R^7$, c) $C_{3-6}$ cycloalkyl, d) aryl or heterocycle, e) HO, f) —$S(O)_mR^{6a}$, or g) —$C(O)NR^6R^7$, 2) aryl or heterocycle, 3) halogen,

4) $OR^6$,

5) $NR^6R^7$,

6) CN,

7) $NO_2$,

8) $CF_3$;

9) —S(O)$_m$R$^{6a}$,
10) —C(O)NR$^6$R$^7$, or
11) C$_3$–C$_6$ cycloalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1; and
u is 4 or 5; or the pharmaceutically acceptable salts thereof.

In a second embodiment of this invention, the inhibitors of farnesyl-protein transferase are illustrated by the formula B:

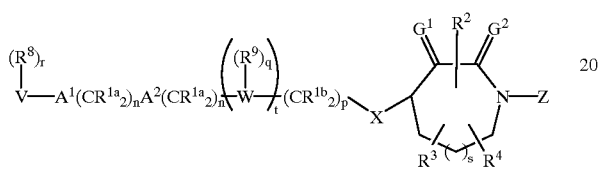

wherein:

R$^{1a}$ and R$^{1b}$ are independently selected from:
 a) hydrogen,
 b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, CN(R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
 c) unsubstituted or substituted C$_1$–C$_6$ alkyl wherein the substituent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$;

R$^2$ and R$^3$ are independently selected from: H; unsubstituted or substituted C$_{1-8}$ alkyl, unsubstituted or substituted C$_{2-8}$ alkenyl, unsubstituted or substituted C$_{2-8}$ alkynyl, unsubstituted or substituted aryl, unsubstituted or substituted heterocycle,

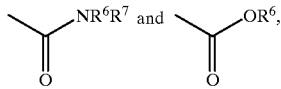

wherein the substituted group is substituted with one or more of:
 1) aryl or heterocycle, unsubstituted or substituted with:
  a) C$_{1-4}$ alkyl,
  b) (CH$_2$)$_p$OR$^6$,
  c) (CH$_2$)$_p$NR$^6$R$^7$,
  d) halogen,
  e) CN,
  f) aryl or heteroaryl,
  g) perfluoro-C$_{1-4}$ alkyl,
  h) SR$^{6a}$, S(O)R$^{6a}$, SO$_2$R$^{6a}$,
 2) C$_{3-6}$ cycloalkyl,
 3) OR$^6$,
 4) SR$^{6a}$, S(O)R$^{6a}$, or SO$_2$R$^{6a}$,
 5) —NR$^6$R$^7$,
 6)
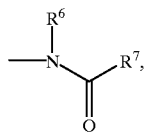
 7)
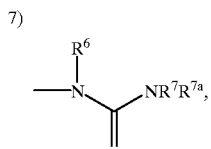
 8)
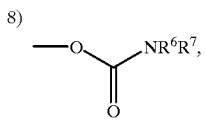
 9)
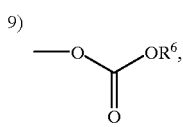
 10)
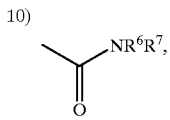
 11) —SO$_2$—NR$^6$R$^7$,
 12)
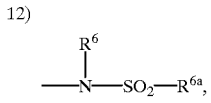
 13)
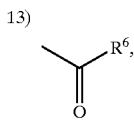
 14)
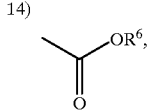

15) N$_3$,
 16) F, or
 17) perfluoro-C$_{1-4}$-alkyl; or

R$^2$ and R$^3$ are attached to the same C atom and are combined to form —(CH$_2$)$_u$— wherein one of the carbon atoms is optionally replaced by a moiety selected from: O, $S(O)_m$, —NC(O)—, and —N(COR$^{10}$)—;

R$^4$ is selected from H and CH$_3$; and any two of R$^2$, R$^3$ and R$^4$ are optionally attached to the same carbon atom;

R$^6$, R$^7$ and R$^{7a}$ are independently selected from: H; C$_{1-4}$ alkyl, C$_{3-6}$ cycloalkyl, heterocycle, aryl, aroyl, heteroaroyl, arylsulfonyl and heteroarylsulfonyl, unsubstituted or substituted with:
   a) C$_{1-4}$ alkoxy,
   b) aryl or heterocycle,
   c) halogen,
   d) HO,
   e)

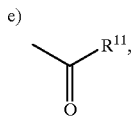

f) —SO$_2$R$^{11}$, or
   g) N(R$^{10}$)$_2$; or

R$^6$ and R$^7$ may be joined in a ring;
R$^7$ and R$^{7a}$ may be joined in a ring;
R$^{6a}$ is selected from: C$_{1-4}$ alkyl, C$_{3-6}$ cycloalkyl, heterocycle and aryl, unsubstituted or substituted with:
   a) C$_{1-4}$ alkoxy,
   b) aryl or heterocycle,
   c) halogen,
   d) HO,
   e)

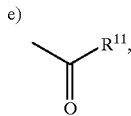

f) —SO$_2$R$^{11}$, or
   g) N(R$^{10}$)$_2$;

R$^8$ is independently selected from:
   a) hydrogen,
   b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$OC(O)—, N$_3$, —N(R$^{10}$)$_2$, or R$^{11}$OC(O)NR$^{10}$—, and
   c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$OC(O)NH—, (R$^{10}$)$_2$NC(O)—, R$^{10}$$_2$N—C(NR$^{10}$)—, CN, R$^{11}$C(O)—, N$_3$, —N(R$^{10}$)$_2$, or R$^{10}$OC(O)NH—;

R$^9$ is selected from:
   a) hydrogen,
   b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
   c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$— and S(O)$_m$;

G$^1$ and G$^2$ are independently oxygen or absent provided that at least one of G$^1$ and G$^2$ is oxygen;

V is selected from:
   a) hydrogen,
   b) heterocycle,
   c) aryl,
   d) C$_1$–C$_{20}$ alkyl wherein from 0 to 4 carbon atoms are replaced with a a heteroatom selected from O, S, and N, and
   e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;
X is a bond, —CH$_2$—, —C(=O)—, or —S(=O)$_m$—;
Z is selected from:
   1) a unsubstituted or substituted group selected from aryl, heteroaryl, arylmethyl, heteroarylmethyl, arylsulfonyl and heteroarylsulfonyl, wherein the substituted group is substituted with one or more of the following:
      a) C$_{1-4}$ alkyl, unsubstituted or substituted with: C$_{1-4}$ alkoxy, NR$^6$R$^7$, C$_{3-6}$ cycloalkyl, aryl, heterocycle, HO, —S(O)$_m$R$^{6a}$, or —C(O)NR$^6$R$^7$,
      b) aryl or heterocycle,
      c) halogen,
      d) OR$^6$,
      e) NR$^6$R$^7$,
      f) CN,
      g) NO$_2$,
      h) CF$_3$;
      i) —S(O)$_m$R$^{6a}$,
      j) —C(O)NR$^6$R$^7$, or
      k) C$_3$–C$_6$ cycloalkyl; and
   2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl,wherein the substituted C$_1$–C$_6$ alkyl and substituted C$_3$–C$_6$ cycloalkyl is substituted with one or two of the following:
      a) C$_{1-4}$ alkoxy,
      b) NR$^6$R$^7$,
      c) C$_{3-6}$ cycloalkyl,
      d) —NR$^6$C(O)R$^7$,
      e) HO,
      f) —S(O)$_m$R$^{6a}$,
      g) halogen, or
      h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1; and
u is 4 or 5; or the pharmaceutically acceptable salts thereof.

In a third embodiment of this invention, the inhibitors of farnesyl-protein transferase are illustrated by the formula C:

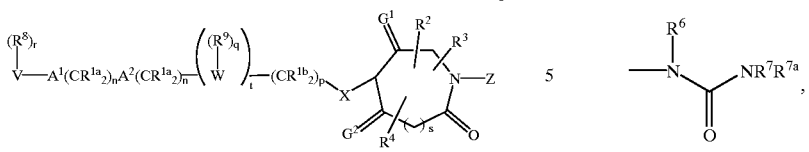

wherein:

$R^{1a}$ and $R^{1b}$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $R^{10}OC(O)$—, $N_3$, —$N(R^{10})_2$, and $R^{11}OC(O)$—$NR^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

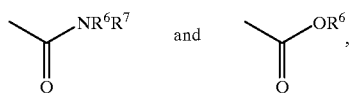

wherein the substituted group is substituted with one or more of:

1) aryl or heterocycle, unsubstituted or substituted with:
 a) $C_{1-4}$ alkyl,
 b) $(CH_2)_pOR^6$,
 c) $(CH_2)_pNR^6R^7$,
 d) halogen,
 e) CN,
 f) aryl or heteroaryl,
 g) perfluoro-$C_{1-4}$ alkyl,
 h) $SR^{6a}$, $S(O)R^{6a}$, $SO_2R^{6a}$, 2) $C_{3-6}$ cycloalkyl,

3) $OR^6$,

4) $SR^{6a}$, $S(O)R^{6a}$, or $SO_2R^{6a}$,

5) —$NR^6R_7$,

6) 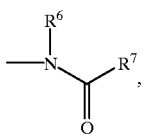

7) 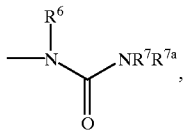

8) 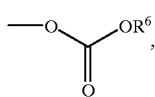

9) 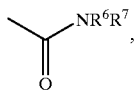

10) 

11) —$SO_2$—$NR^6R^7$,

12) 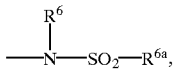

13) 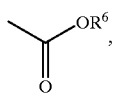

14) 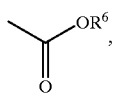

15) $N_3$,

16) F, or 17) perfluoro-$C_{1-4}$-alkyl; or $R^2$ and $R^3$ are attached to the same C atom and are combined to form —$(CH_2)_u$— wherein one of the carbon atoms is optionally replaced by a moiety selected from: O, $S(O)_m$, —NC(O)—, and —$N(COR^{10})$—;

$R^4$ is selected from H and $CH_3$; and any two of $R^2$, $R^3$ and $R^4$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl and heteroarylsulfonyl, unsubstituted or substituted with:

a) $C_{1-4}$ alkoxy, b) aryl or heterocycle,
c) halogen,
d) HO,
e)

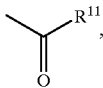

f) —SO$_2$R$^{11}$, or
g) N(R$^{10}$)$_2$; or

R$^6$ and R$^7$ may be joined in a ring;
R$^7$ and R$^{7a}$ may be joined in a ring;
R$^{6a}$ is selected from: C$_{1-4}$ alkyl, C$_{3-6}$ cycloalkyl, heterocycle and aryl, unsubstituted or substituted with:
a) C$_{1-4}$ alkoxy,
b) aryl or heterocycle,
c) halogen,
d) HO,
e)

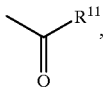

f) —SO$_2$R$^{11}$, or
g) N(R$^{10}$)$_2$;

R$^8$ is independently selected from:
a) hydrogen,
b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$_{10}$)—, CN, R$^{10}$C(O)—, N$_3$, —N(R$^{10}$)$_2$, or R$^{10}$OC(O)NH—;

R$^9$ is selected from:
a) hydrogen,
b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;
R$^{11}$ is independently selected from C$_1$–C$_6$ alkyl and aryl;
A$^1$ and A$^2$ are independently selected from: a bond, —CH═CH—, —C≡C—, —C(O)—, —C(O)NR$^{10}$—, —NR$^{10}$C(O)—, O, —NR$^{10}$)—, —S(O)$_2$N(R$^{10}$)—, —N(R$^{10}$)S(O)$_2$— and S(O)$_m$;
G$^1$ and G$^2$ are independently oxygen or absent, provided that if G$^1$ is oxygen then G$^2$ is absent and if s=0, G$^1$ is oxygen;
V is selected from:
a) hydrogen,
b) heterocycle,
c) aryl,
d) C$_1$–C$_{20}$ alkyl wherein from 0 to 4 carbon atoms are replaced with a a heteroatom selected from O, S, and N, and
e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;
X is a bond, —CH$_2$—, —C(═O)—, or —S(═O)$_m$—;
Z is selected from:
1) a unsubstituted or substituted group selected from aryl, heteroaryl, arylmethyl, heteroarylmethyl, arylsulfonyl and heteroarylsulfonyl, wherein the substituted group is substituted with one or more of the following:
a) C$_{1-4}$ alkyl, unsubstituted or substituted with:
C$_{1-4}$ alkoxy, NR$^6$R$^7$, C$_{3-6}$ cycloalkyl, aryl, heterocycle, HO, —S(O)$_m$R$^{6a}$, or —C(O)NR$^6$R$^7$,
b) aryl or heterocycle,
c) halogen,
d) OR$^6$,
e) NR$^6$R$^7$,
f) CN,
g) NO$_2$,
h) CF$_3$;
i) —S(O)$_m$R$^{6a}$,
j) —C(O)NR$^6$R$^7$, or
k) C$_3$–C$_6$ cycloalkyl; and
2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
a) C$_{1-4}$ alkoxy,
b) NR$^6$R$^7$,
c) C$_{3-6}$ cycloalkyl,
d) —NR$^6$C(O)R$^7$,
e) HO,
f) —S(O)$_m$R$^{6a}$,
g) halogen, or
h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 1;
t is 0 or 1; and
u is 4 or 5; or the pharmaceutically acceptable salts thereof.

In a preferred embodiment of this invention, the inhibitors of farnesyl-protein transferase are illustrated by the formula B:

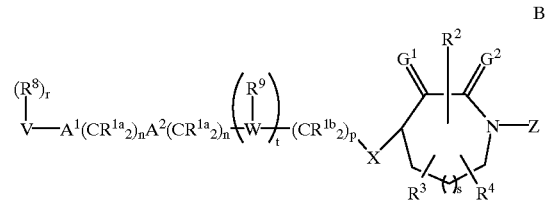

wherein:
R$^{1a}$ is independently selected from: hydrogen and C$_1$–C$_6$ alkyl;
R$^{1b}$ is independently selected from:

a) hydrogen,
b) aryl, heterocycle, cycloalkyl, $R^{10}O—$, $—N(R^{10})_2$ or $C_2–C_6$ alkenyl, and
c) unsubstituted or substituted $C_1–C_6$ alkyl wherein the substitutent on the substituted $C_1–C_6$ alkyl is selected from unsubstituted or substituted aryl, heterocycle, cycloalkyl, alkenyl, $R^{10}O—$ and $—N(R^{10})_2$;

$R^3$ and $R^4$ are independently selected from H and $CH_3$;

$R^2$ is H;

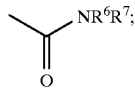

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

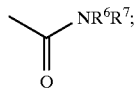

and any two of $R^2$, $R^3$, and $R^4$ are optionally attached to the same carbon atom;

$R^6$, $R^7$ and $R^{7a}$ are independently selected from:
H; $C_{1-4}$ alkyl, $C_{3-6}$ cycloalkyl, aryl and heterocycle, unsubstituted or substituted with:
  a) $C_{1-4}$ alkoxy,
  b) halogen, or
  c) aryl or heterocycle;

$R^{6a}$ is selected from:
$C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^8$ is independently selected from:
a) hydrogen,
b) $C_1–C_6$ alkyl, $C_2–C_6$ alkenyl, $C_2–C_6$ alkynyl, $C_1–C_6$ perfluoroalkyl, F, Cl, $R^{10}O—$, $R^{10}C(O)NR^{10}—$, CN, $NO_2$, $(R^{10})_2N—C(NR^{10})—$, $R^{10}C(O)—$, $—N(R^{10})_2$, or $R^{11}OC(O)NR^{10}—$, and
c) $C_1–C_6$ alkyl substituted by $C_1–C_6$ perfluoroalkyl, $R^{10}O—$, $R^{10}C(O)NR^{10}—$, $(R^{10})_2N—C(NR^{10})—$, $R^{10}C(O)—$, $—N(R^{10})_2$, or $R^{11}OC(O)NR^{10}—$;

$R^9$ is selected from:
a) hydrogen,
b) $C_2–C_6$ alkenyl, $C_2–C_6$ alkynyl, $C_1–C_6$ perfluoroalkyl, F, Cl, $R^{10}O—$, $R^{11}S(O)_m—$, $R^{10}C(O)NR^{10}—$, CN, $NO_2$, $(R^{10})_2N—C(NR^{10})—$, $R^{10}C(O)—$, $—N(R^{10})_2$, or $R^{11}OC(O)NR^{10}—$, and
c) $C_1–C_6$ alkyl unsubstituted or substituted by $C_1–C_6$ perfluoroalkyl, F, Cl, $R^{10}O—$, $R^{11}S(O)_m—$, $R^{10}C(O)NR^{10}—$, CN, $(R^{10})_2N—C(NR^{10})—$, $R^{10}C(O)—$, $—N(R^{10})_2$, or $R^{11}OC(O)NR^{10}—$;

$R^{10}$ is independently selected from hydrogen, $C_1–C_6$ alkyl, benzyl and aryl;

$R^{11}$ is independently selected from $C_1–C_6$ alkyl and aryl;

$A^1$ and $A^2$ are independently selected from: a bond, $—CH=CH—$, $—C\equiv C—$, $—C(O)—$, $—C(O)NR^{10}—$, O, $—N(R^{10})—$ and $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1–C_{20}$ alkyl wherein from 0 to 4 carbon atoms are replaced with a a heteroatom selected from O, S, and N, and
e) $C_2–C_{20}$ alkenyl, and provided that V is not hydrogen if $A^1$ is $S(O)_m$ and V is not hydrogen if $A^1$ is a bond, n is 0 and $A^2$ is $S(O)_m$;

$G^1$ is absent;

$G^2$ is oxygen;

W is a heterocycle selected from pyrrolidinyl, imidazolyl, pyridinyl, thiazolyl, pyridonyl, 2-oxopiperidinyl, indolyl, quinolinyl and isoquinolinyl;

X is $—CH_2—$ or $—C(=O)—$;

Z is selected from:
1) a unsubstituted or substituted group selected from aryl, heteroaryl, arylmethyl, heteroarylmethyl, arylsulfonyl and heteroarylsulfonyl, wherein the substituted group is substituted with one or more of the following:
  a) $C_{1-4}$ alkyl, unsubstituted or substituted with: $C_{1-4}$ alkoxy, $NR^6R^7$, $C_{3-6}$ cycloalkyl, aryl, heterocycle, HO, $—S(O)_mR^{6a}$, or $—C(O)NR^6R^7$,
  b) aryl or heterocycle,
  c) halogen,
  d) $OR^6$,
  e) $NR^6R^7$,
  f) CN,
  g) $NO_2$,
  h) $CF_3$;
  i) $—S(O)_mR^{6a}$,
  j) $—C(O)NR^6R^7$, or
  k) $C_3–C_6$ cycloalkyl; and
2) unsubstituted $C_1–C_6$ alkyl, substituted $C_1–C_6$ alkyl, unsubstituted $C_3–C_6$ cycloalkyl or substituted $C_3–C_6$ cycloalkyl, wherein the substituted $C_1–C_6$ alkyl and substituted $C_3–C_6$ cycloalkyl is substituted with one or two of the following:
  a) $C_{1-4}$ alkoxy,
  b) $NR^6R^7$,
  c) $C_{3-6}$ cycloalkyl,
  d) $—NR^6C(O)R^7$,
  e) HO,
  f) $—S(O)_mR^{6a}$,
  g) halogen, or
  h) perfluoroalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 0 or 1; and
u is 4 or 5; or the pharmaceutically acceptable salts thereof.

A preferred embodiment of the compounds of this invention are illustrated by the formula D:

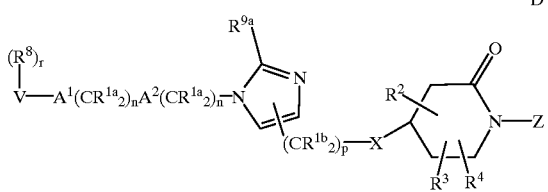

wherein:

$R^{1a}$ is selected from: hydrogen and $C_1$–$C_6$ alkyl;

$R^{1b}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^3$ and $R^4$ independently selected from H and $CH_3$;

$R^2$ is selected from H;

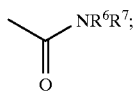

and $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

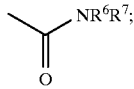

and $R^2$, $R^3$ and $R^4$ are optionally attached to the same carbon atom;

$R^6$ and $R^7$ are independently selected from:
H; $C_{1-4}$ alkyl, $C_{3-6}$ cycloalkyl, aryl and heterocycle, unsubstituted or substituted with:
a) $C_{1-4}$ alkoxy,
b) halogen, or
c) aryl or heterocycle;

$R^{6a}$ is selected from:
$C_{1-4}$ alkyl and $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)$NR^{10}$—, O, —$N(R^{10})$— and $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is —$CH_2$— or —C(=O)—;

Z is selected from:
1) a unsubstituted or substituted group selected from aryl, heteroaryl, arylmethyl, heteroarylmethyl, arylsulfonyl and heteroarylsulfonyl, wherein the substituted group is substituted with one or more of the following:
a) $C_{1-4}$ alkyl, unsubstituted or substituted with: $C_{1-4}$ alkoxy, $NR^6R^7$, $C_{3-6}$ cycloalkyl, aryl, heterocycle, HO, —$S(O)_mR^{6a}$, or —$C(O)NR^6R^7$,
b) aryl or heterocycle,
c) halogen,
d) $OR^6$,
e) $NR^6R^7$,
f) CN,
g) $NO_2$,
h) $CF_3$;
i) —$S(O)_mR^{6a}$,
j) —$C(O)NR^6R^7$, or
k) $C_3$–$C_6$ cycloalkyl; and
2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
a) $C_{1-4}$ alkoxy,
b) $NR^6R^7$,
c) $C_{3-6}$ cycloalkyl,
d) —$NR^6C(O)R^7$,
e) HO,
f) —$S(O)_mR^{6a}$,
g) halogen, or
h) perfluoroalkyl;

m is 0, 1 or 2;

n is 0, 1, 2, 3 or 4;

p is 0, 1, 2, 3 or 4; and r is 0 to 5, provided that r is 0 when V is hydrogen; or the pharmaceutically acceptable salts thereof.

In another preferred embodiment of this invention, the inhibitors of farnesyl-protein transferase are illustrated by the formula E:

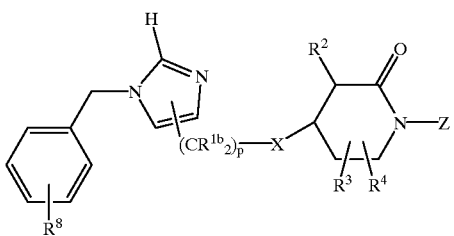

wherein:
$R^{1b}$ is independently selected from:
 a) hydrogen,
 b) aryl, heterocycle, cycloalkyl, $R^{10}O-$, $-N(R^{10})_2$ or $C_2-C_6$ alkenyl, and
 c) $C_1-C_6$ alkyl unsubstituted or substituted by aryl, heterocycle, cycloalkyl, alkenyl, $R^{10}O-$, or $-N(R^{10})_2$;

$R^3$ and $R^4$ independently selected from H and $CH_3$;
$R^2$ is selected from H;

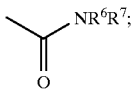

and $C_{1-5}$ alkyl, unbranched or branched, unsubstituted or substituted with one or more of:
 1) aryl,
 2) heterocycle,
 3) $OR^6$,
 4) $SR^{6a}$, $SO_2R^{6a}$, or
 5)

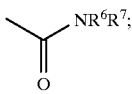

and $R^2$, $R^3$ and $R^4$ are optionally attached to the same carbon atom;

$R^6$ and $R^7$ are independently selected from:
 H; $C_{1-4}$ alkyl, $C_{3-6}$ cycloalkyl, aryl and heterocycle, unsubstituted or substituted with:
  a) $C_{1-4}$ alkoxy,
  b) halogen, or
  c) aryl or heterocycle;

$R^{6a}$ is selected from:
 $C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^8$ is independently selected from:
 a) hydrogen,
 b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
 c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, benzyl and aryl;
$R^{11}$ is independently selected from $C_1-C_6$ alkyl and aryl;
X is $-CH_2-$ or $-C(=O)-$;
Z is selected from:
 1) a unsubstituted or substituted group selected from aryl, heteroaryl, arylmethyl, heteroarylmethyl, arylsulfonyl and heteroarylsulfonyl, wherein the substituted group is substituted with one or more of the following:
  a) $C_{1-4}$ alkyl, unsubstituted or substituted with: $C_{1-4}$ alkoxy, $NR^6R^7$, $C_{3-6}$ cycloalkyl, aryl, heterocycle, HO, $-S(O)_mR^{6a}$, or $-C(O)NR^6R^7$,
  b) aryl or heterocycle,
  c) halogen,
  d) $OR^6$,
  e) $NR^6R^7$,
  f) CN,
  g) $NO_2$,
  h) $CF_3$;
  i) $-S(O)_mR^{6a}$,
  j) $-C(O)NR^6R^7$, or
  k) $C_3-C_6$ cycloalkyl; and
 2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
  a) $C_{1-4}$ alkoxy,
  b) $NR^6R^7$,
  c) $C_{3-6}$ cycloalkyl,
  d) $-NR^6C(O)R^7$,
  e) HO,
  f) $-S(O)_mR^{6a}$,
  g) halogen, or
  h) perfluoroalkyl;

m is 0, 1 or 2; and
p is 0, 1, 2, 3 or 4; or the pharmaceutically acceptable salts thereof.

In another preferred embodiment of this invention, the inhibitors of farnesyl-protein transferase are illustrated by the formula F:

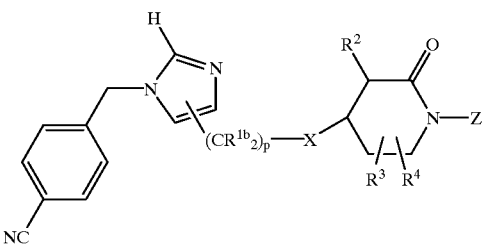

wherein:
$R^{1b}$ is independently selected from:
 a) hydrogen,
 b) aryl, heterocycle, cycloalkyl, $R^{10}O-$, $-N(R^{10})_2$ or $C_2-C_6$ alkenyl, and
 c) $C_1-C_6$ alkyl unsubstituted or substituted by aryl, heterocycle, cycloalkyl, alkenyl, $R^{10}O-$, or $-N(R^{10})_2$;

$R^3$ and $R^4$ independently selected from H and $CH_3$;

$R^2$ is selected from H;

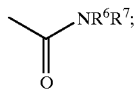

and $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

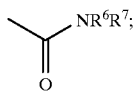

and $R^2$, $R^3$ and $R^4$ are optionally attached to the same carbon atom;
$R^6$ and $R^7$ are independently selected from:
  H; $C_{1-4}$ alkyl, $C_{3-6}$ cycloalkyl, aryl and heterocycle, unsubstituted or substituted with:
    a) $C_{1-4}$ alkoxy,
    b) halogen, or
    c) aryl or heterocycle;
$R^{6a}$ is selected from:
  $C_{1-4}$ alkyl and $C_{3-6}$ cycloalkyl, unsubstituted or substituted with:
    a) $C_{1-4}$ alkoxy,
    b) halogen, or
    c) aryl or heterocycle;
$R^{10}$ is independently selected from hydrogen, $C_1$–$C_6$ alkyl, benzyl and aryl;
$R^{11}$ is independently selected from $C_1$–$C_6$ alkyl and aryl;
X is —$CH_2$— or —C(=O)—;
Z is selected from:
  1) a unsubstituted or substituted group selected from aryl, heteroaryl, arylmethyl, heteroarylmethyl, arylsulfonyl and heteroarylsulfonyl, wherein the substituted group is substituted with one or more of the following:
    a) $C_{1-4}$ alkyl, unsubstituted or substituted with:
       $C_{1-4}$ alkoxy, $NR^6R^7$, $C_{3-6}$ cycloalkyl, aryl, heterocycle, HO, —$S(O)_mR^{6a}$, or —$C(O)NR^6R^7$,
    b) aryl or heterocycle,
    c) halogen,
    d) $OR^6$,
    e) $NR^6R^7$,
    f) CN,
    g) $NO_2$,
    h) $CF_3$;
    i) —$S(O)_mR^{6a}$,
    j) —$C(O)NR^6R^7$, or
    k) $C_3$–$C_6$ cycloalkyl; and
  2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
    a) $C_{1-4}$ alkoxy,
    b) $NR^6R^7$,
    c) $C_{3-6}$ cycloalkyl,
    d) —$NR^6C(O)R^7$,
    e) HO,
    f) —$S(O)_mR^{6a}$,
    g) halogen, or
    h) perfluoroalkyl;
m is 0, 1 or 2; and
p is 0, 1, 2, 3 or 4; or the pharmaceutically acceptable salts thereof.

Examples of the compounds of this invention are as follows:
  4-[5-(4-Cyanobenzyl)imidazol-1-ylmethyl]-1-phenyl-2-piperidinone
  4-[2-{5-(4-Cyanobenzyl)imidazol-1-yl}ethyl]-1-phenyl-2-piperidinone
  4-[2-{1-(4-Cyanobenzyl)-5-imidazolyl}ethyl]-1-phenyl-2-piperidinone
  (±)cis-4-[2-{1-(4-Cyanobenzyl)-5-imidazolyl}ethyl]-3-methyl-1-phenyl-2-piperidinone
  (±)trans-4-[2-{1-(4-Cyanobenzyl)-5-imidazolyl}ethyl]-3-methyl-1-phenyl-2-piperidinone
  4-[2-{1-(4-Cyanobenzyl)-5-imidazolyl}carbonyl]-1-phenyl-2-piperidinone and
  Ethyl 1-[3-(4-cyanobenzyl)-3H-imidazol-4-ylmethyl]-3-oxo-4-(3-methylbenzyl)piperidine-4-carboxylate or a pharmaceutically acceptable salt or optical isomer thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^2$ and $R^3$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

As used herein in the definition of $R^6$, $R^{6a}$, $R^7$ and $R^{7a}$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substitutents in addition to the point of attachment to the rest of the compound.

As used herein in the definition of $R^{1a}$ and $R^{1b}$, the term substituted aryl includes moieties containing from 1 to 3 substitutents in addition to the point of attachment to the rest of the compound. Preferably, such substitutents are selected from the group which includes but is not limited to F, Cl, Br, $CF_3$, $NH_2$, $N(C_1-C_6$ alkyl$)_2$, $NO_2$, CN, $(C_1-C_6$ alkyl$)O$—, —OH, $(C_1-C_6$ alkyl$)S(O)_m$—, $(C_1-C_6$ alkyl$)C(O)NH$—, $H_2N$—C(NH)—, $(C_1-C_6$ alkyl$)C(O)$—, $(C_1-C_6$ alkyl$)OC(O)$—, $N_3$,$(C_1-C_6$ alkyl$)OC(O)NH$—, phenyl, pyridyl, imidazolyl, oxazolyl, isoxazolyl, thiazolyl, thienyl, furyl, isothiazolyl and $C_1-C_{20}$ alkyl.

When $R^2$ and $R^3$ are combined to form —(CH$_2$)$_u$—, cyclic moieties are formed. Examples of such cyclic moieties include, but are not limited to:

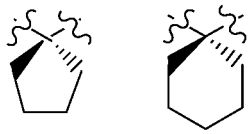

In addition, such cyclic moieties may optionally include a heteroatom(s). Examples of such heteroatom-containing cyclic moieties include, but are not limited to:

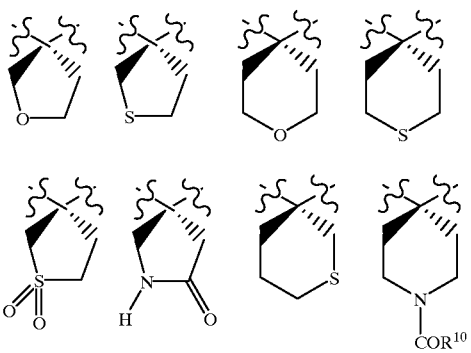

Lines drawn into the ring systems from substituents (such as from $R^2$, $R^3$, $R^4$ etc.) mean that the indicated bond may be attached to any of the substitutable ring carbon atoms. It is understood that the carbon containing the moiety —C(=O)—Y is substitutable with a second substituent $R^2$, $R^3$, $R^4$ or $R^5$.

When substituents $G^1$ and/or $G^2$ are "absent," the ring carbons to which $G^1$ and/or $G^2$ are attached are understood to be substituted with two hydrogen atoms and are considered substitutable ring carbon atoms, and are therefore optionally substituted with a substituent selected from $R^2$, $R^3$, $R^4$ and $R^5$.

Preferably, $R^{1a}$ and $R^{1b}$ are independently selected from: hydrogen, —N(R$^{10}$)$_2$, R$^{10}$C(O)NR$^{10}$— or unsubstituted or substituted $C_1$–$C_6$ alkyl wherein the substituent on the substituted $C_1$–$C_6$ alkyl is selected from unsubstituted or substituted phenyl, —N(R$^{10}$)$_2$, R$^{10}$)— and R$^{10}$C(O)NR$^{10}$—.

Preferably, $R^2$ is selected from: H,

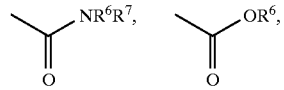

and an unsubstituted or substituted group, the group selected from $C_{1-8}$ alkyl, $C_{2-8}$ alkenyl and $C_{2-8}$ alkynyl; wherein the substituted group is substituted with one or more of:

1) aryl or heterocycle, unsubstituted or substituted with:
   a) $C_{1-4}$ alkyl,
   b) (CH$_2$)$_p$OR$^6$,
   c) (CH$_2$)$_p$NR$^6$R$^7$,
   d) halogen,
2) $C_{3-6}$ cycloalkyl,
3) OR$^6$,
4) SR$^{6a}$, S(O)R$^{6a}$, SO$_2$R$^{6a}$,
5) —NR$^6$R$^7$,
6)

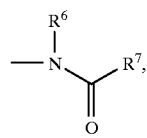

7)

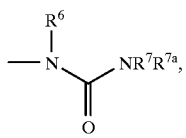

8)

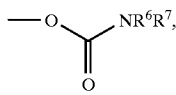

9)

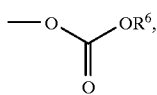

10)

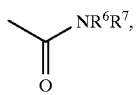

11) —SO$_2$—NR$^6$R$^7$,

12)

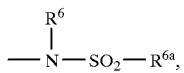

13)

14)

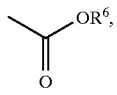

15) N$_3$, or
16) F.

Preferably, R$^3$ is selected from: hydrogen and C$_1$–C$_6$ alkyl.

Preferably, R$^4$ is hydrogen.

Preferably, R$^6$, R$^7$ and R$^{7a}$ is selected from: hydrogen, unsubstituted or substituted C$_1$–C$_6$ alkyl, unsubstituted or substituted aryl and unsubstituted or substituted cycloalkyl.

Preferably, R$^{6a}$ is unsubstituted or substituted C$_1$–C$_6$ alkyl, unsubstituted or substituted aryl and unsubstituted or substituted cycloalkyl.

Preferably, R$^9$ is hydrogen or methyl. Most preferably, R$^a$ is hydrogen.

Preferably, R$^{10}$ is selected from H, C$_1$–C$_6$ alkyl and benzyl.

Preferably, A$^1$ and A$^2$ are independently selected from: a bond, —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, V is selected from hydrogen, heterocycle and aryl. More preferably, V is phenyl.

Preferably, Y is selected from unsubstituted or substituted phenyl, unsubstituted or substituted naphthyl, unsubstituted or substituted pyridyl, unsubstituted or substituted furanyl and unsubstituted or substituted thienyl. More preferably, Y is unsubstituted or substituted phenyl.

Preferably, Z is selected from unsubstituted or substituted phenyl, unsubstituted or substituted naphthyl, unsubstituted or substituted pyridyl, unsubstituted or substituted furanyl, unsubstituted or substituted thienyl, unsubstituted or substituted C$_1$–C$_6$ alkyl and unsubstituted or substituted C$_3$–C$_6$ cycloalkyl. More preferably, Z is unsubstituted or substituted phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, in compounds of the formula A, G$^1$ is oxygen and G$^2$ is absent.

Preferably, in compounds of the formula B, G$^2$ is oxygen and G$^1$ is absent.

Preferably, in compounds of the formula C, G$^1$ is oxygen and G$^2$ is absent.

Preferably, n and r are independently 0, 1, or 2.
Preferably p is 1, 2 or 3.
Preferably s is 0.
Preferably t is 1.
Preferably, the moiety

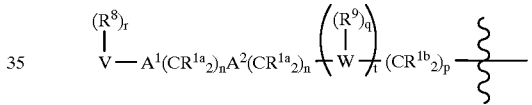

is selected from:

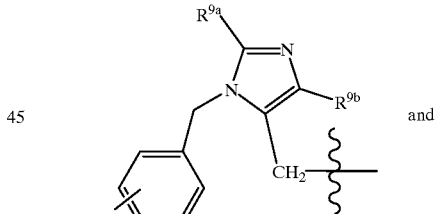

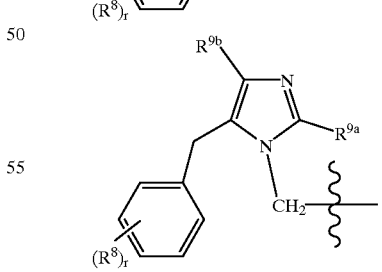

It is intended that the definition of any substituent or variable (e.g., R$^{1a}$, R$^9$, n, etc.) at a particular location in a molecule be independent of its definitions elsewhere in that molecule. Thus, —N(R$^{10}$)$_2$ represents —NH$_2$, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–14, in addition to other standard manipulations such as ester hydrolysis, cleavage of protecting groups, etc., as may be known in the literature or exemplified in the experimental procedures. Substituents R and $R^a$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–14:

The requisite intermediates are in some cases commercially available, or can be prepared according to literature procedures, for the most part. A general synthesis of multiply substituted piperidinones is illustrated in Scheme 1. Thus, a suitably substituted bromoacetonitrile is treated with the sodium salt of diethylmalonate to provide the diester I. Intermediate I is itself deprotonated and alkylated to provide the triester II, which, upon catalytic hydrogenation spontaneously cyclizes to the lactam III. Acidic rearragngement provides the substituted piperidone IV.

As shown is Scheme 2, the piperidone nitrogen may be arylated by employing a triaryl bismuth-copper coupling. The resulting diester Va can then be converted to the acid VIa and the aldehyde VIIa by procedures well known in the art. Scheme 3 illustrates the analogous preparation of the piperidone having an alkyl substitutent on the ring nitrogen.

The aldehyde intermediates VII can undergo a Wittig coupling with a protected imidazole to provide compound IX, which can then be catalytically reduced to the intermediate X (Scheme 4). Intermediate X can be deprotected to provide the instant compound XI or it can be further alkylated to eventually provide the instant compound XII.

Synthesis of compounds of the invention that have an alternate connectivity of the piperidinon-4-ylethyl to the preferred imidazolyl moiety is illustrated in Scheme 4a. The Scheme illustrates use of a suitably substituted protected piperidine XIII, which is either commercially avaiable or may be prepared by techniques known in the art, as the precursor to the 2-piperidinone XV. The nitrogen of intermediate XV may then be functionalized and the suitably substituted imidazolyl moiety incorporated via nucleophilic displacement.

Schemes 4b and 4c illustrate syntheses of suitably substituted homologous 4-hydroxymethyl 2-piperidinones, that may be utilized in the reactions illustrated in Scheme 4a, starting with commercially available materials.

Schemes 4d and 4e illustrate alternate syntheses of the homologous piperidinon-4-ylmethyl-1-imidazolyl compounds starting with the previously described intermediate IV.

The key intermediates whose syntheses are illustrated in Schemes 2, 3a, 3b and 3c may also be utilized in the subsequent reactions.

Scheme 5 illustrates the preparation of the instant compound wherein the linker between the piperidone and the heterocyclic substitutent is a carbonyl. Thus the protected imidazolyl Grignard XVI is reacted with the key intermediate VII to provide the secondary alcohol, which can be oxidized and alkylated as illustrated above to provide the instant compound XVII. Scheme 6 illustrates the analogous synthesis of the instant compound XVIII wherein the heterocyclic moity is linked to the piperidone carbon by an acetyl linker.

The carboxylic acid VI can be converted to the phosphonium salt XIX which can then be coupled to a variety of aldehydes, such as XX, as shown in Scheme 7. The aldehydes can be prepared by standard procedures, such as that described by O. P. Goel, U. Krolls, M. Stier and S. Kesten in *Organic Syntheses*, 1988, 67, 69–75), from the appropriate amino acid. The coupling reaction provides the unsaturated intermediate, which is catalytically reduced to the bisprotected diamine XXI. The product XXI can be deprotected to give the instant compound XXII with trifluoroacetic acid in methylene chloride. The final product XXII is isolated in the salt form, for example, as a trifluoroacetate, hydrochloride or acetate salt, among others. The product diamine XXII can further be selectively protected to obtain XXIII, which can subsequently be reductively alkylated with a second aldehyde to obtain XXIV. Removal of the protecting group, and conversion to cyclized products such as the dihydroimidazole XXV can be accomplished by literature procedures.

If the phosphonium XIX is coupled with with an aldehyde which also has a protected hydroxyl group, such as XXVI in Scheme 8, the protecting groups can be subsequently removed to unmask the hydroxyl group (Schemes 8, 9). The alcohol can be oxidized under standard conditions to e.g. an aldehyde, which can then be reacted with a variety of organometallic reagents such as Grignard reagents, to obtain secondary alcohols such as XXIX. In addition, the fully deprotected amino alcohol XXX can be reductively alkylated (under conditions described previously) with a variety of aldehydes to obtain secondary amines, such as XXXI (Scheme 9), or tertiary amines.

The Boc protected amino alcohol XXVII can also be utilized to synthesize 2-aziridinylmethylpiperidones such as XXXII (Scheme 10). Treating XXVII with 1,1'-sulfonyldiimidazole and sodium hydride in a solvent such as dimethylformamide led to the formation of aziridine XXXII. The aziridine reacted in the presence of a nucleophile, such as a thiol, in the presence of base to yield the ring-opened product XXXIII.

In addition, as illustrated in Scheme 11, the phosphonium XVIII can be reacted with aldehydes derived from amino acids such as O-alkylated tyrosines, according to standard procedures, to obtain compounds such as XXXIII. When R' is an aryl group, catalytic hydrogenation of XXXIII also unmasks the phenol, and the amine group is then deprotected with acid to produce XXXV. Alternatively, when R' is not an aryl group, XXXV is an O-alkylated phenolic amines.

Schemes 12–15 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

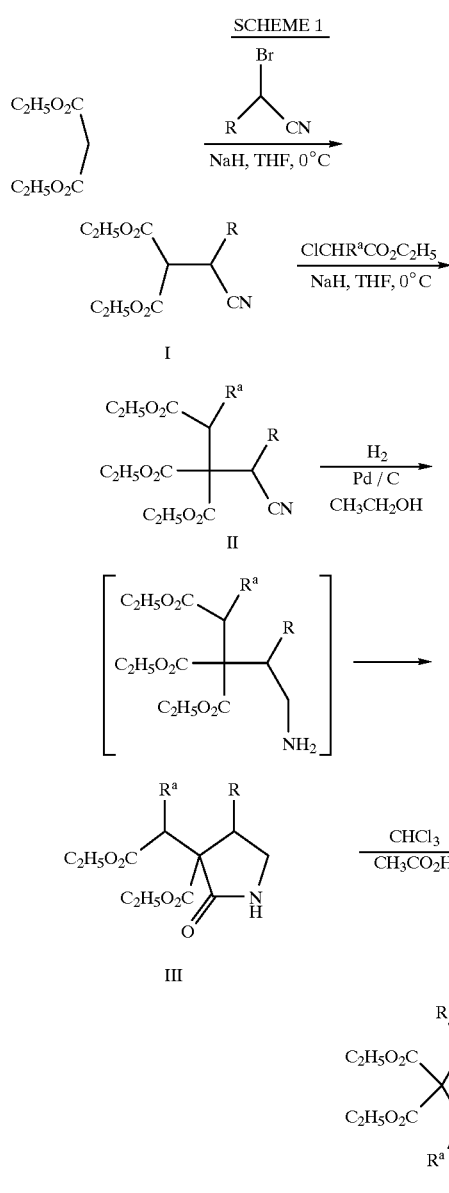

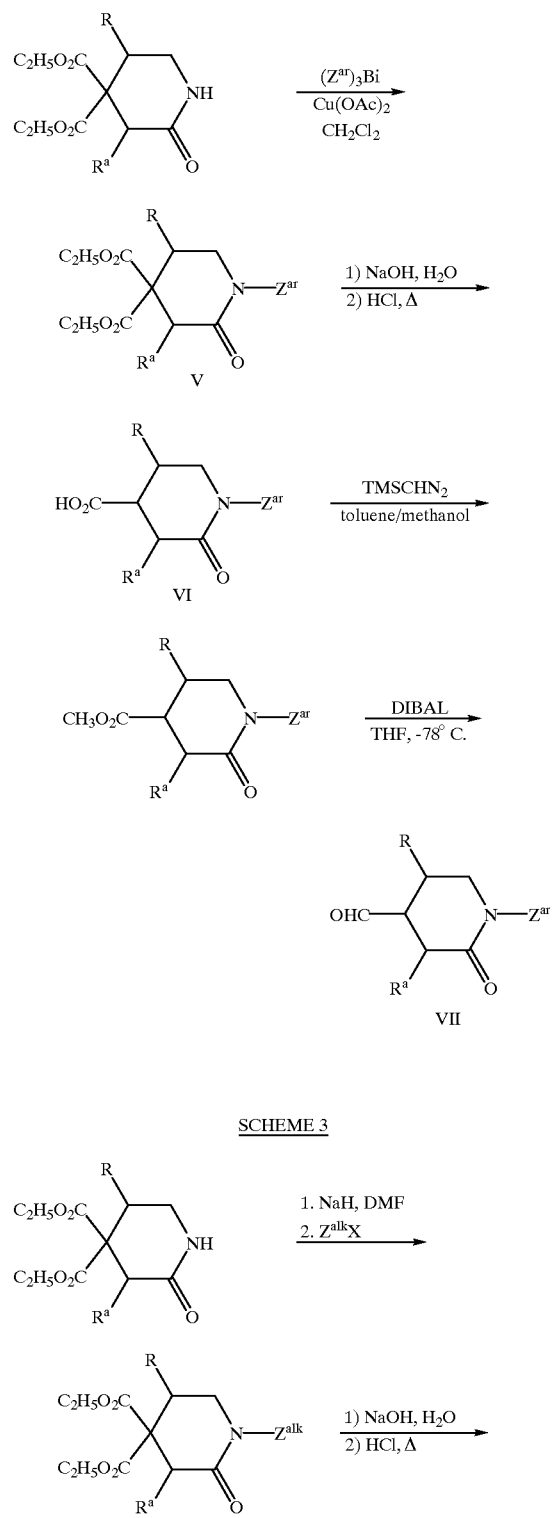

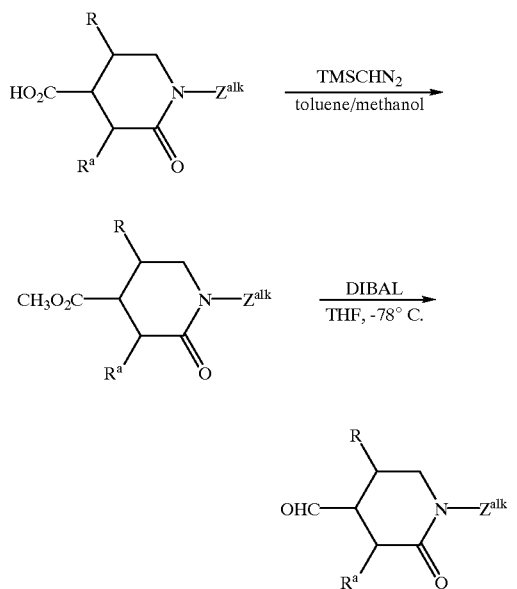
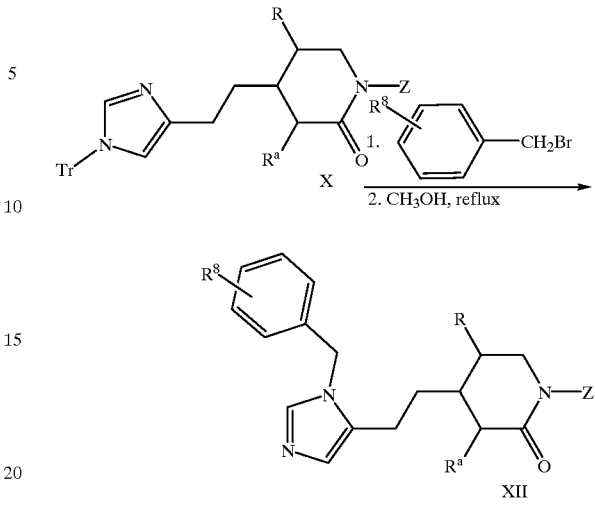
SCHEME 4
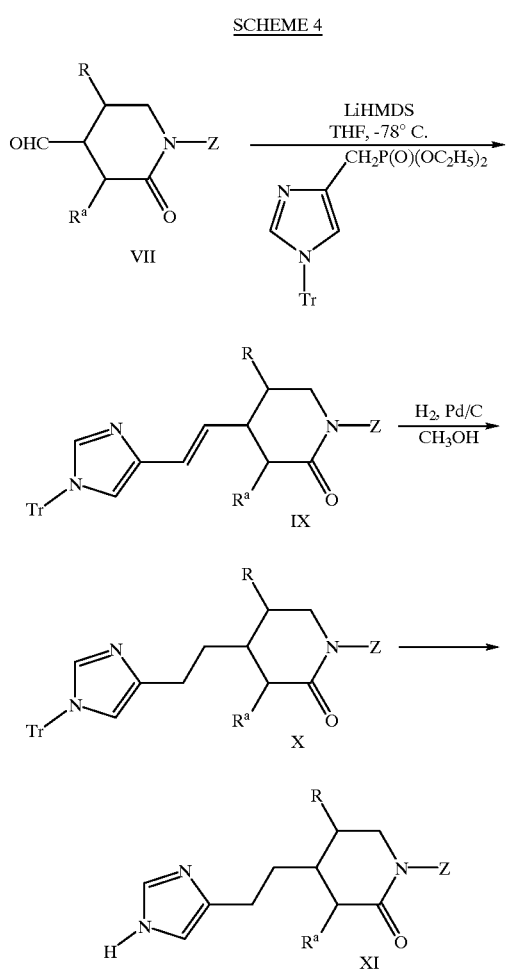
SCHEME 4a
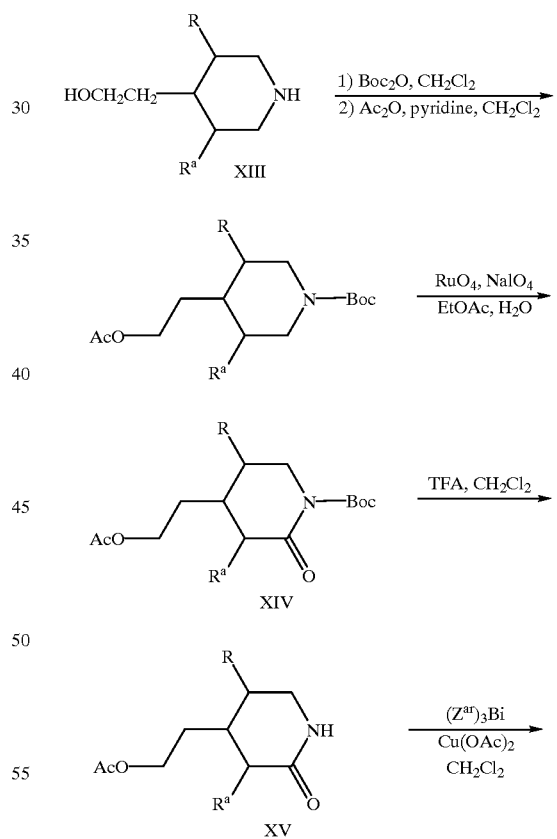

-continued
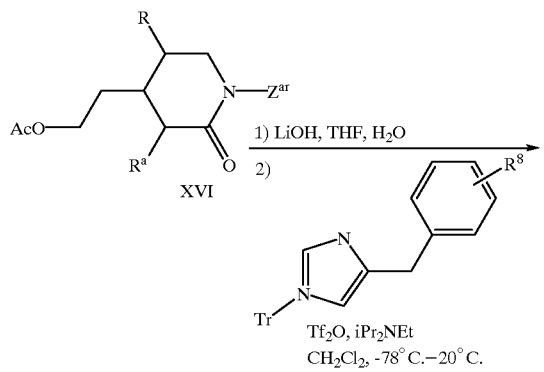
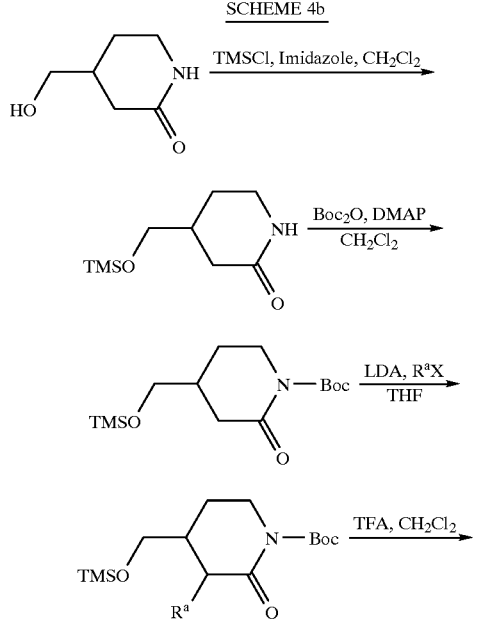
SCHEME 4c
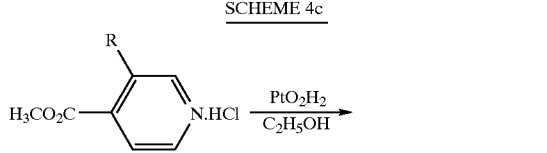
-continued
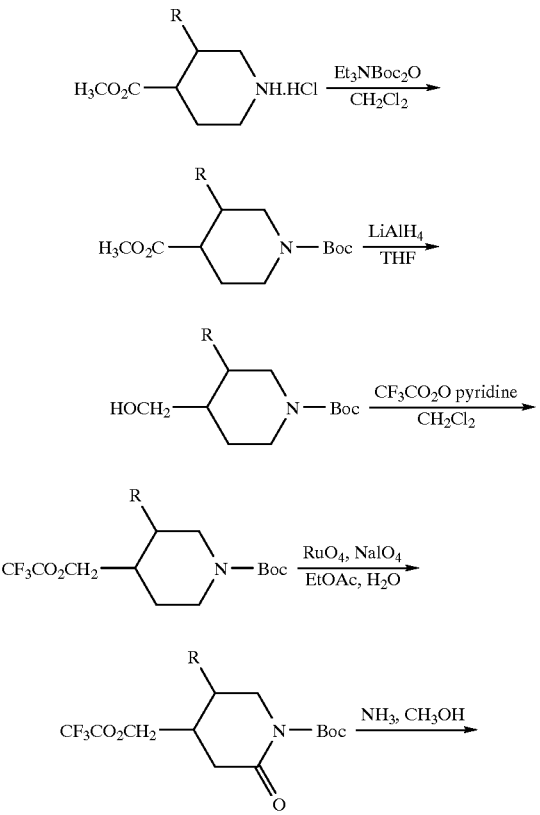
SCHEME 4d
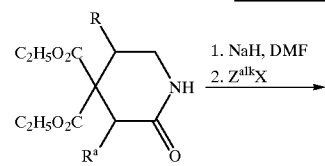
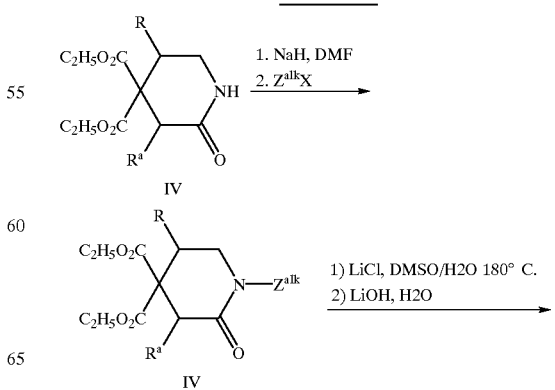

-continued
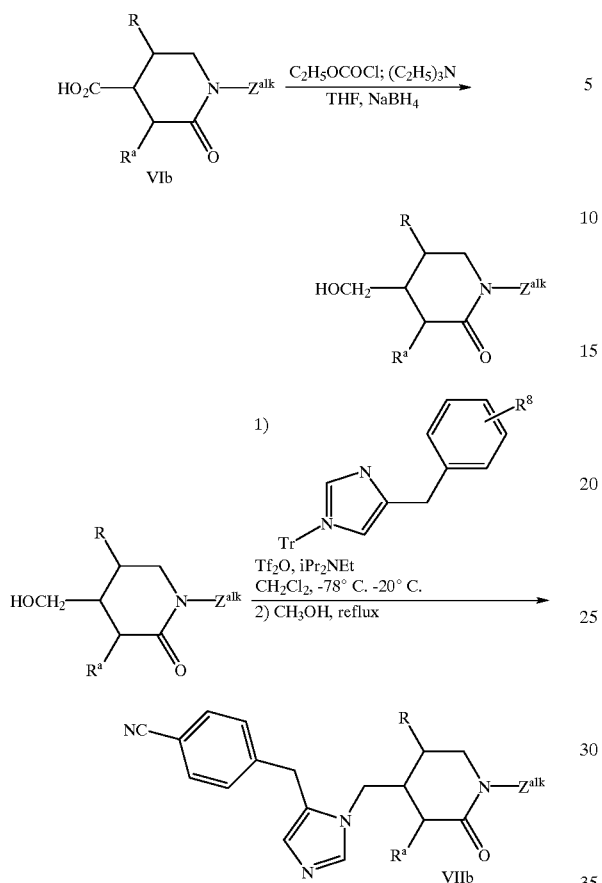
SCHEME 4e
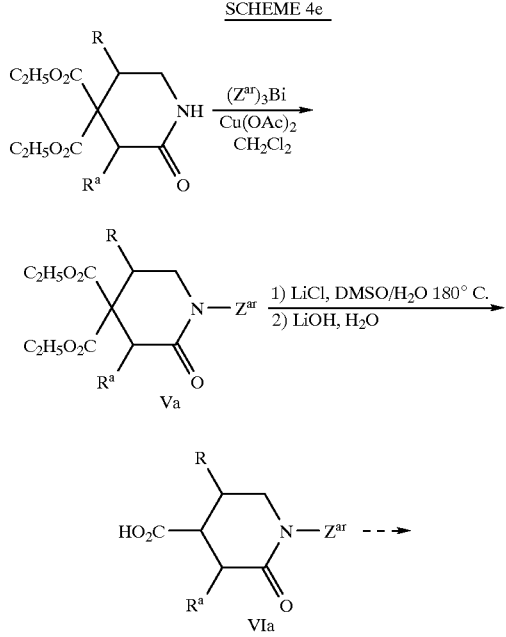
SCHEME 5
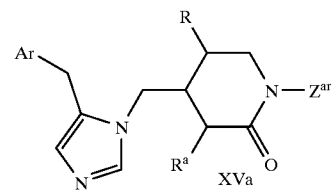
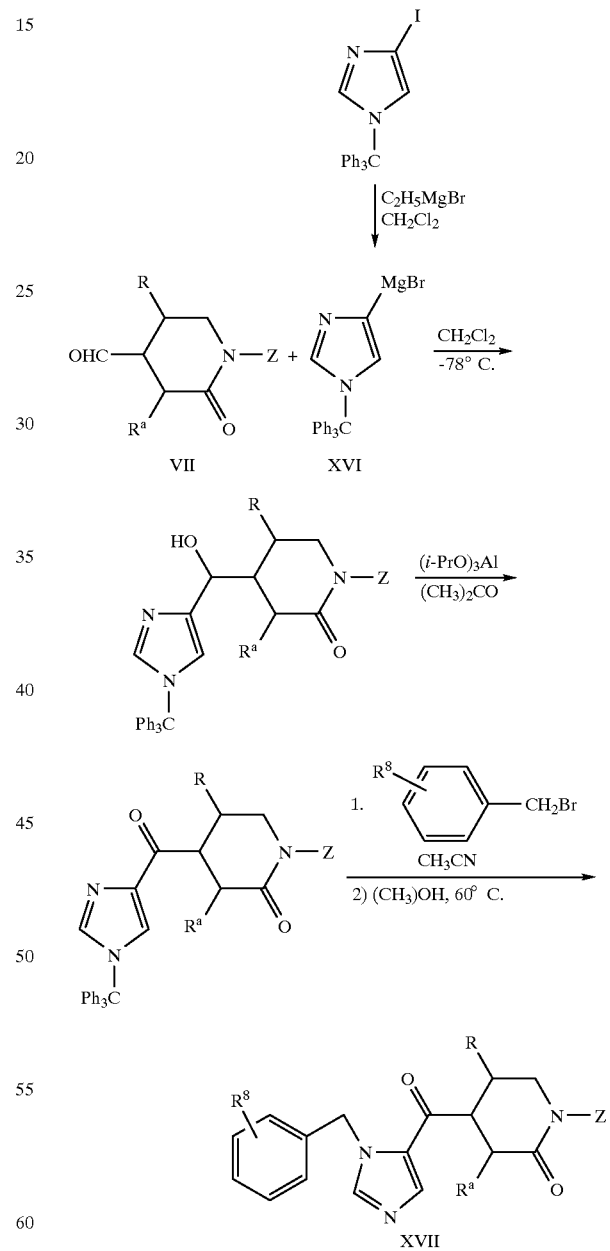

SCHEME 6
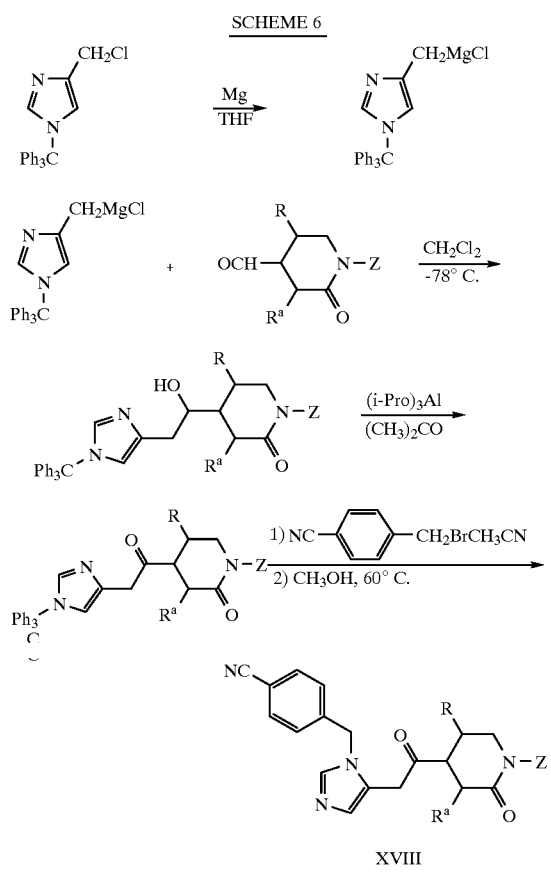
SCHEME 7
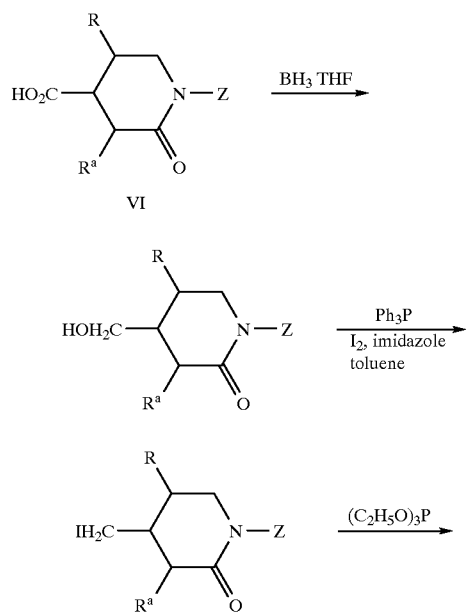
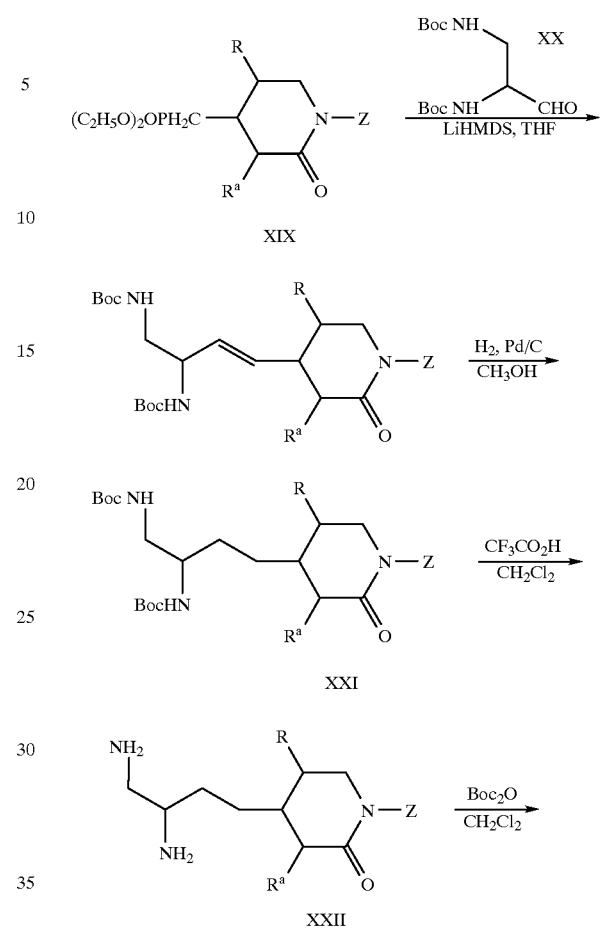
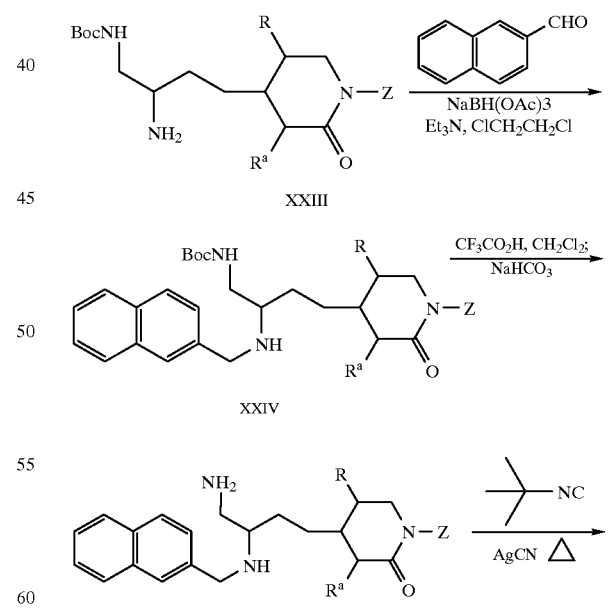

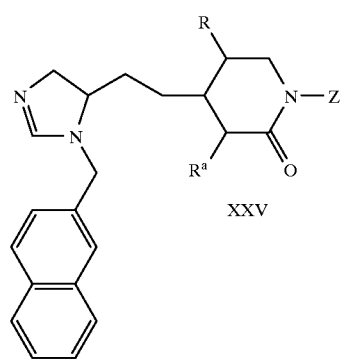
XXV
SCHEME 8
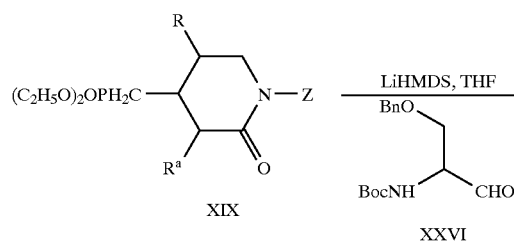
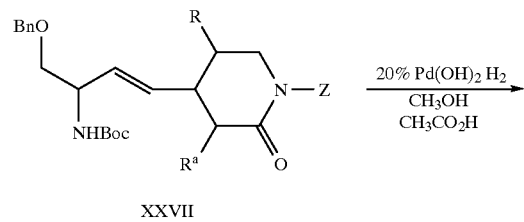
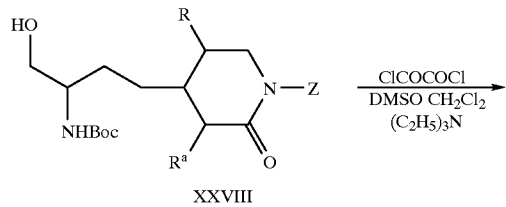
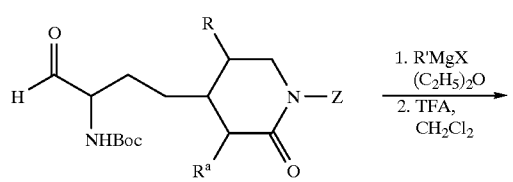
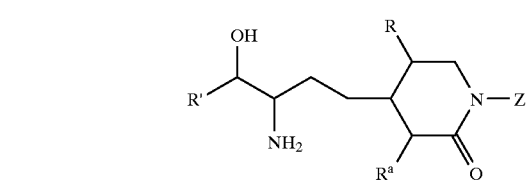
SCHEME 9
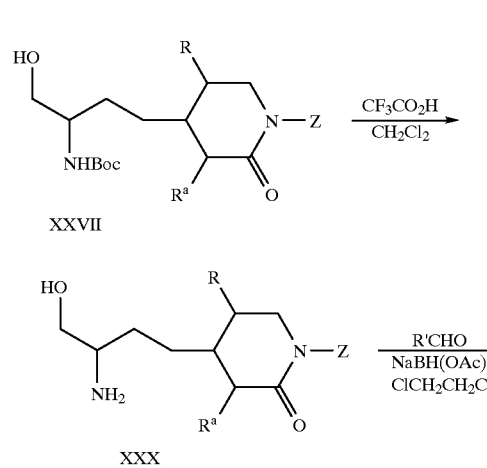
SCHEME 10
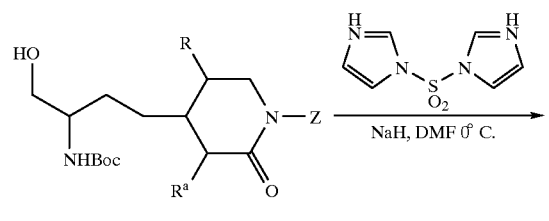
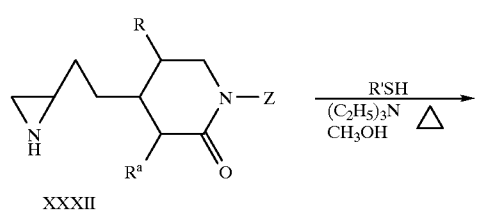
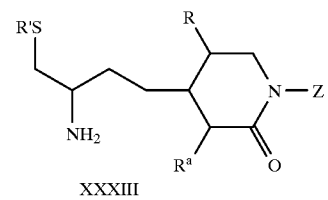

SCHEME 11
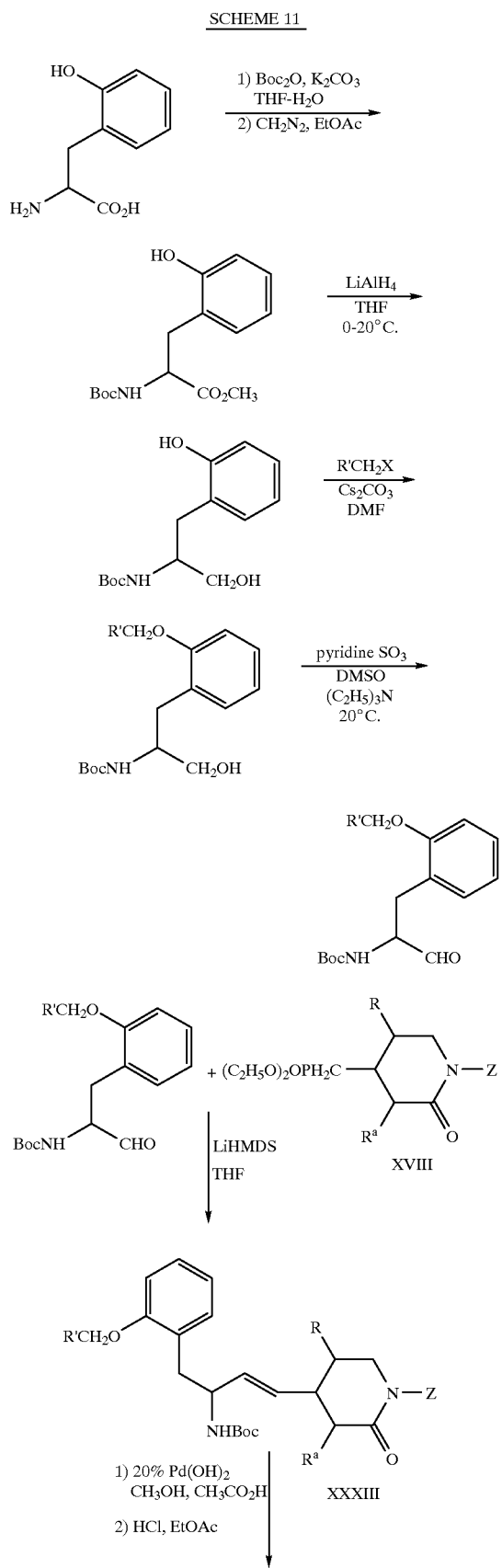
1) 20% Pd(OH)₂
   CH₃OH, CH₃CO₂H
2) HCl, EtOAc
XXXIII
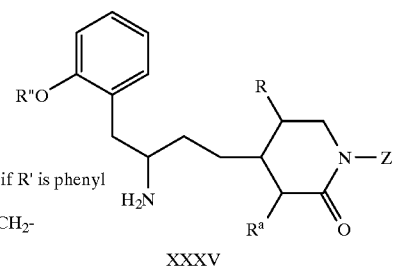
R" = H, if R' is phenyl
or
R" is R'CH₂-
XXXV
REACTION SCHEME 12
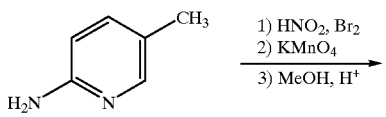
1) HNO₂, Br₂
2) KMnO₄
3) MeOH, H⁺
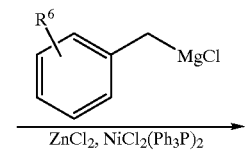
ZnCl₂, NiCl₂(Ph₃P)₂
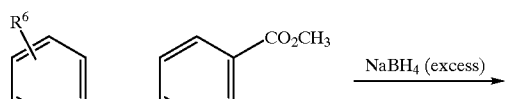
NaBH₄ (excess)
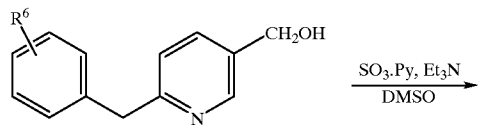
SO₃·Py, Et₃N
DMSO
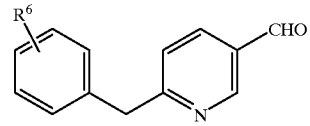
REACTION SCHEME 13
1. EtO(CO)Cl
2. R⁶—C₆H₄—CH₂MgCl
   Zn, CuCN
3. S, xylene, heat
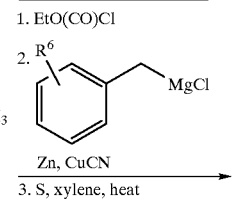

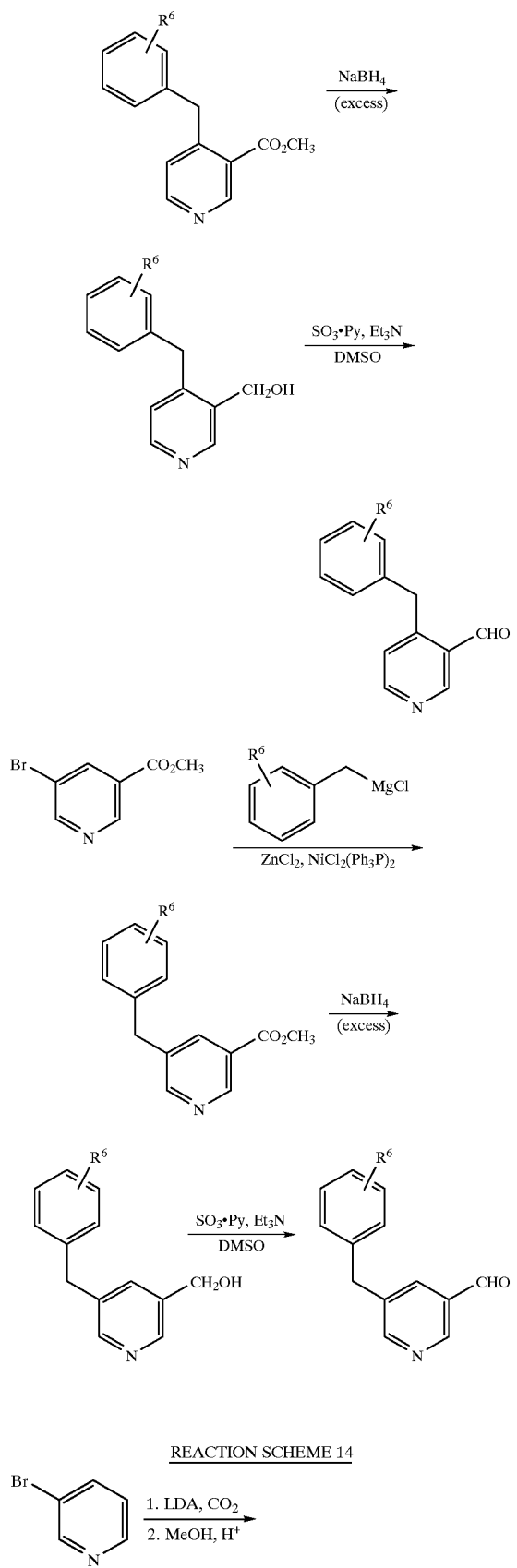
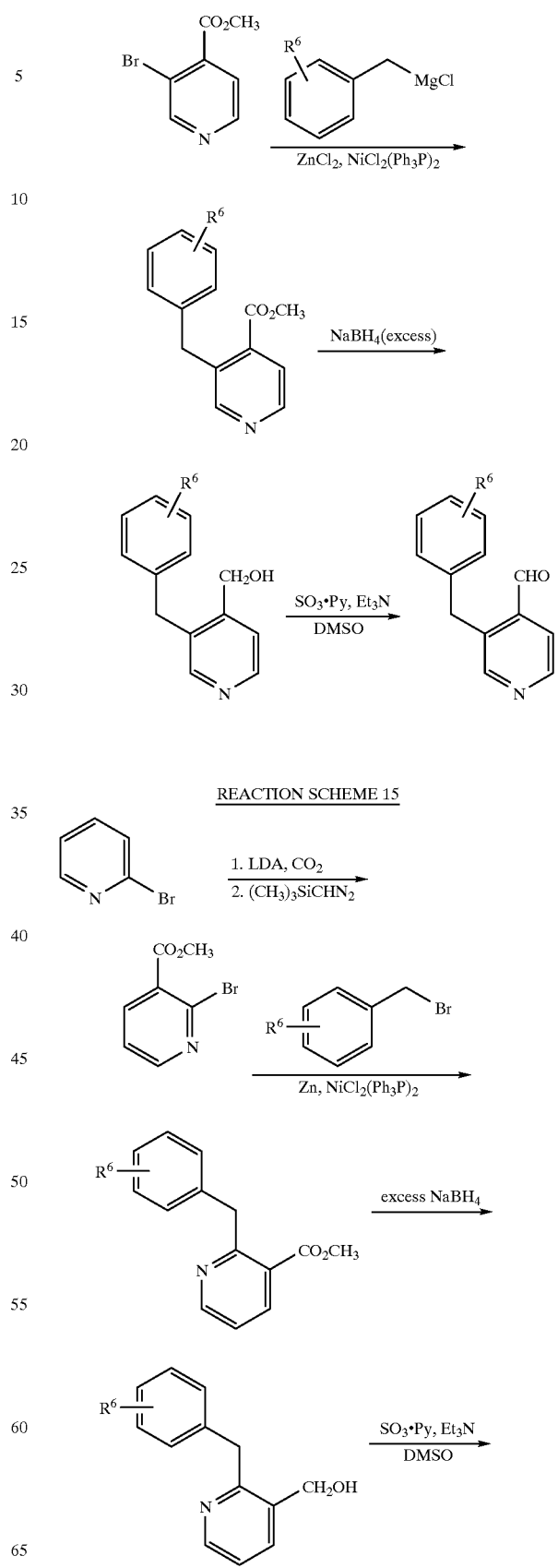
REACTION SCHEME 15
REACTION SCHEME 14

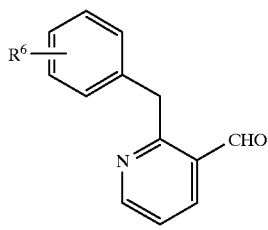

REACTION SCHEME 16

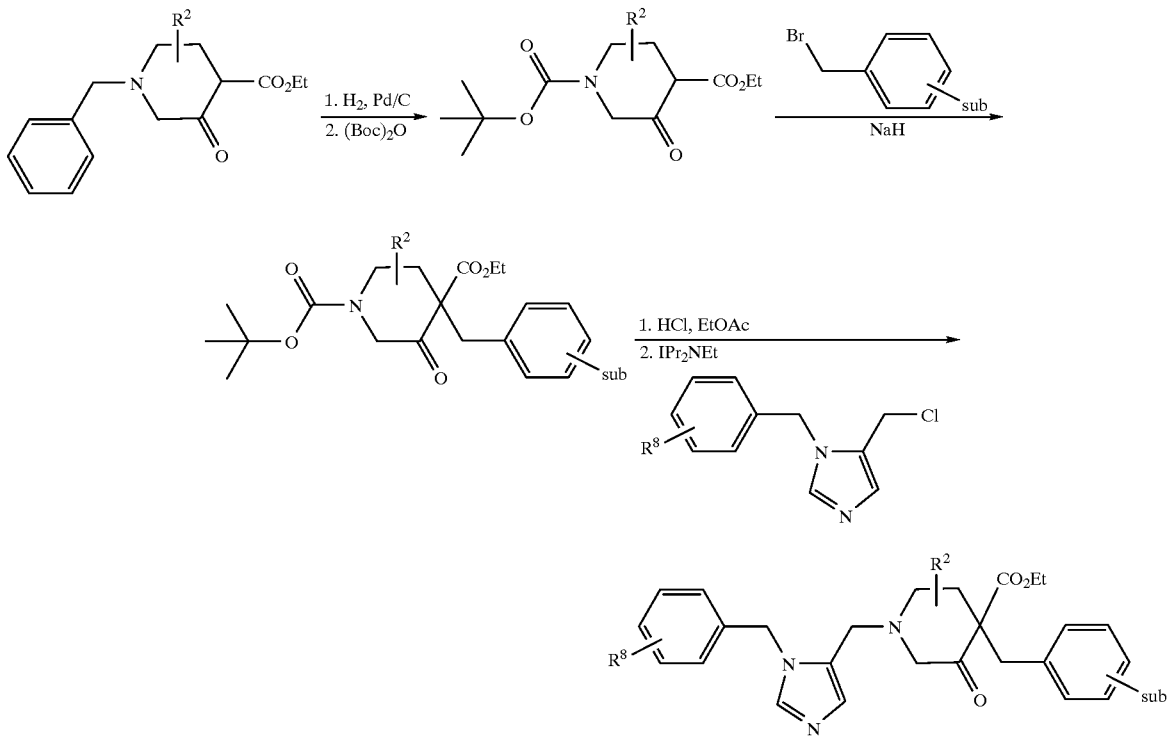

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995)).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

4-[5-(4-Cyanobenzyl)imidazol-1-ylmethyl]-1-phenyl-2-piperidinone hydrochloride

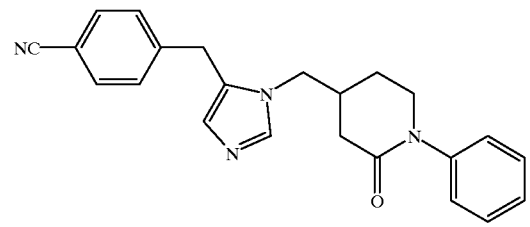

Step A: 1-Phenyl-2-piperidinone-4,4-dicarboxylic acid diethyl ester

2-Piperidinone-4,4-dicarboxylic acid diethyl ester, prepared as described in U.S. Pat. No. 4,870,173, is dissolved in methylene chloride and treated with triphenylbismuth (1.5 equivalents), copper(II)acetate (1.5 equivalents) and triethylamine (1.5 equivalents) and stirred for 17 h at 20° C. in dichloromethane (60 mL). The reaction mixture was adsorbed onto silica gel and chromatographed to provide the title compound.

Step B: 1-Phenyl-2-piperidinone-4-carboxylic acid ethyl ester

The product from Step A (4.78 g, 14.98 mmol) was dissolved in DMSO (90 mL) containing water (0.27 mL, 14.98 mmol) and lithium chloride (1.27 g, 29.96 mmol). The reaction was heated at 180° C. under argon for 3.5 h. The cooled reaction mixture was partitioned between ethyl acetate and water. Ther organic phase was washed with saturated brine, and dried over magnesium sulfate. The title compound was isolated as a white solid following chromatography on silica gel with 50% ethyl acetate in hexane.

Step C: 1-Phenyl-2-piperidinone-4-carboxylic acid

The product from Step B (2.60 g, 10.52 mmol) was dissolved in THF (60 mL) and lithium hydroxide hydrate (2.15 g, 51 mmol) and water (10 mL) were added. The reaction was stirred for 4 h at room temperature, at which time 6N aqueous hydrogen chloride solution was added to adjust the pH to 1, and the product extracted with ethyl acetate. The organic phase was dried with magnesium sulfate, filtered and evaporated to reveal the title compound.

Step D: 4-Hydroxymethyl-1-phenyl-2-piperidinone

The product from Step C (1.57 g, 7.16 mmol) was dissolved in THF (30 mL) and triethylamine (1.20 mL, 8.59 mmol) was added. The reaction was cooled to 0° C. under argon, and ethyl chloroformate added (0.82 mL, 8.59 mmol). The reaction was stirred for 1 h at 0° C., and then sodium borohydride was added (0.81 g, 21.5 mmol). After 3 h, the reaction was quenched by the addition of saturated sodium bicarbonate solution. The aqueous phase was extracted with ethyl acetate. The organic phase was washed with 2% aqueous potassium hydrogen sulfate and saturated brine. After drying over magnesium sulfate, the crude product was chromatographed on silica gel with 5% methanol in chloroform. The title compound was obtained as a white solid.

Step E: 1-Trityl-4-(4-cyanobenzyl)-imidazole.

To a suspension of activated zinc dust (3.57 g, 54.98 mmol) in THF (50 mL) was added dibromoethane (0.315 mL, 3.60 mmol) and the reaction stirred under argon at 20° C. The suspension was cooled to 0° C. and α-bromo-p-toluinitrile (9.33 g, 47.6 mmol) in THF (100 mL) was added dropwise over a period of 10 min. The reaction was then allowed to stir at 20° C. for 6 h and bis(triphenylphosphine) Nickel II chloride (2.4 g, 3.64 mmol) and 4-iodotrityl imidazole (15.95 g, 36.6 mmol) were added in one portion. The resulting mixture was stirred 16 h at 20° C. and then quenched by addition of saturated ammonium chloride solution (100 mL) and the mixture stirred for 2 h. Saturated sodium bicarbonate solution was added to give a pH of 8 and the solution was extracted with ethyl acetate (2×250 mL), dried with magnesium sulfate, and the solvent evaporated in vacuo. The residue was chromatographed on silica gel with 0–20% ethyl acetate in methylene chloride to afford the title compound as a white solid.

$^1$H NMRδCDCl$_3$ (7.54 (2H,d, J=7.9Hz), 7.38(1H,s), 7.36–7.29 (11H,m), 7.15–7.09(6H,m), 6.58(1H,s), and 3.93 (2H,s)ppm.

Step F: 4-[5-(4-Cyanobenzyl)imidazol-1-ylmethyl]-1-phenyl-2-piperidinone hydrochloride The product from Step D (0.205 g, 1.00 mmol) and the product from Step E (0.425 g, 1.00 mmol) were dissolved in methylene chloride (2 mL) containing diisopropylethylamine (0.191 mL, 1.10 mmol) and cooled to −78° C. under argon. Trifluoromethane sulfonic anhydride was added (0.173 mL, 1.03 mmol) and the reaction stirred at −78° C. for 1 h, followed by warming to room temperature over 2 h. The solvent was evaporated, and the residue dissolved in methanol. After refluxing for 30 min, the methanol was evaporated, and the residue is partitioned between ethyl acetate and saturated sodium bicarbonate solution. The organic phase is washed with saturated brine, dried over magnesium sulfate, filtered and concentrated. The free base product was chromatographed on silica gel with 3% methanol in methylene chloride follwed by 7% 9:1 methanol:ammonium hydroxide in methylene chloride. The title compound was obtained after conversion to the hydrochloride salt. FAB ms: 371 (M+1). Anal. Calc for C$_{23}$H$_{22}$N$_4$O·HCl·H$_2$O, C, 65.01; H, 5.93; N,13.19. Found: C, 64.77; H, 5.89; N, 13.11.

Example 2

4-[2-{5-(4-Cyanobenzyl)imidazol-1-yl}ethyl]-1-phenylpiperidin-2-one hydrochloride

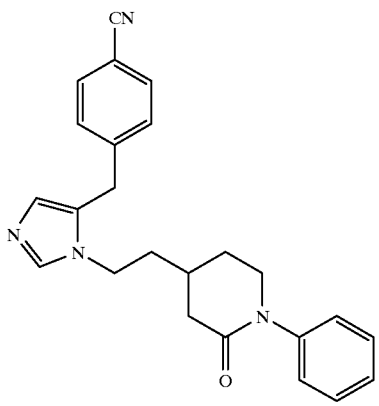

Step A: 1-tert-Butoxycarbonyl-4-hydroxyethylpiperidine 4-(2-Hydroxyethyl)piperidine (4.91 g, 38.06 mmol) was dissolved in methylene chloride (80 mL) and di-tert-butyl dicarbonate (8.71 g, 39.96 mmol) was added. After stirring at room temperature overnight, saturated sodium bicarbonate was added, and the layers separated. The organic phase was washed with 2% potassium hydrogen sulfate, saturated sodium carbonate and saturated brine, then dried over magnesium sulfate. The title compound was obtained as a yellow oil.

Step B: 4-(2-Acetoxyethyl)-1-tert-butoxycarbonylpiperidine

The product from Step A (6.62 g, 28.90 mmol) was dissolved in methylene chloride (50 mL) containing pyridine (5.8 mL, 72.27 mmol). The reaction was cooled to 0° C. under argon, and acetic anhydride added (3.3 mL, 34.68 mmol). The reaction was stirred overnight at room temperature. Saturated sodium bicarbonate solution was added, and the layers separated. The organic phase was washed with 10% aqueous hydrogen chloride, saturated sodium bicarbonate solution, and saturated brine. The organic phase was dried over magnesium sulfate. The title compound was obtained as an oil.

Step C: 4-(2-Acetoxyethyl)-1-tert-butoxycarbonylpiperidin-2-one

The product from Step B (0.275 g, 1.01 mmol) was dissolved in ethyl acetate (5 mL). A solution of sodium periodate in water (0.5 g in 5 mL) and ruthenium tetroxide (13 mg, 0.10 mmol) was added, and the heterogeneous reaction stirred vigorously overnight at room temperature. An additional portion of sodium periodate in water was added (0.5 g in 5 mL) and the reaction stirred overnight. The reaction was quenched with 10% sodium thiosulfate, and filtered through celite. The phases were separated, and the organic phase dried over magnesium sulfate. Filtration and evaporation gave the title compound.

Step D: 4-(2-Acetoxyethyl)piperidin-2-one

The product from Step C is dissolved in 2:1 methylene chloride and trifluoroacetic acid. The reaction is stirred for 1 h, and evaporated, giving the title compound.

Step E: 4-(2-Acetoxyethyl)-1-phenylpiperidin-2-one

The product from Step D is dissolved in methylene chloride and treated with triphenylbismuth (1.5 equivalents), copper(II)acetate (1.5 equivalents) and triethylamine (1.5 equivalents) and stirred for 17 h at 20° C. in dichloromethane (60 mL). The reaction mixture is adsorbed onto silica gel and chromatographed to provide the title compound.

Step F: 4-(2-Hydroxyethyl)-1-phenylpiperidin-2-one

The product from Step E is hydrolyzed according to the procedure described in Example 1, Step C, giving the title compound.

Step G: 4-[2-{5-(4-Cyanobenzyl)imidazol-1-yl}ethyl]-1-phenylpiperidin-2-one hydrochloride The product from Step F (1 eq) and the product from Example 1, Step E (1 eq) were dissolved in methylene chloride containing diisopropylethylamine, cooled to −78° C. under argon and treated with trifluoromethane sulfonic anhydride as described in Example 1, Step F. After methanolysis, the title compound was isolated by chromatography on silica gel.

Example 3

4-[2-{1-(4-Cyanobenzyl)-5-imidazolyl}ethyl]-1-phenyl-2-piperidinone hydrochloride

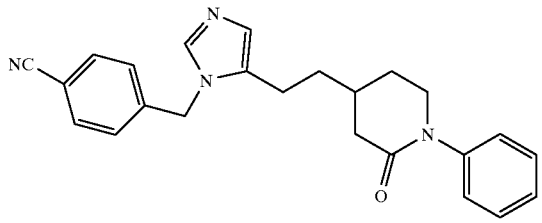

Step A: 1-Phenyl-2-piperidinone-4,4-dicarboxylic acid diethyl ester

2-Piperidinone-4,4-dicarboxylic acid diethyl ester, prepared as described in U.S. Pat. No. 4,870,173, is dissolved in methylene chloride and treated with triphenylbismuth (1.5 equivalents), copper(II)acetate (1.5 equivalents) and triethylamine (1.5 equivalents) and stirred for 17 h at 20° C. in dichloromethane (60 mL). The reaction mixture is adsorbed onto silica gel and chromatographed to provide the title compound.

Step B: 1-Phenyl-2-piperidinone-4,4-dicarboxylic acid

The product from Step A is dissolved in methanol and 5% aqueous sodium hydroxide added. When the hydrolysis is complete, 6 N aqueous hydrochloric acid is added to obtain pH 1, and the solution extracted with ethyl acetate. The organic phase is washed with saturated brine, dried over magnesium sulfate, filtered and concentrated to provide the title compound.

Step C: 1-Phenyl-2-piperidinone-4-carboxylic acid

The product from step B is dissolved in toluene and refluxed for 6 h. The reaction is cooled and concentrated to provide the title compound.

Step D: 1-Phenyl-2-piperidinone-4-carboxylic acid methyl ester

The product from Step C is dissolved in 10% methanol in toluene, and trimethylsilyldiazomethane added. The reaction is quenched with acetic acid and concentrated. The residue is partitioned between ethyl acetate and saturated sodium bicarbonate solution. The organic phase is washed with saturated brine, dried over magnesium sulfate, filtered and concentrated to provide the title compound.

Step E: 4-Formyl-1-phenyl-2-piperidinone

The product from Step D is dissolved in THF and cooled to −78° C. under nitrogen. A solution of diisobutylaluminum hydride (1 eq.) in toluene is added dropwise. After 30 min, the reaction is quenched with saturated sodium potassium tartrate solution. The mixture is extracted with ethyl acetate, and the organic phase washed with saturated brine, and dried over $MgSO_4$. Filtration and concentration provides the title compound.

Step F: 4-Hydroxymethyl-1-triphenylmethylimidazole

To a solution of 4-(hydroxymethyl)imidazole hydrochloride (35.0 g, 260 mmol) in 250 mL of dry DMF at room temperature is added triethylamine (90.6 mL, 650 mmol). A white solid precipitated from the solution. Chlorotriphenylmethane (76.1 g, 273 mmol) in 500 mL of DMF is added dropwise. The reaction mixture is stirred for 20 hours, poured over ice, filtered, and washed with ice water. The resulting product is slurried with cold dioxane, filtered, and dried in vacuo to provide the titled product as a white solid which is sufficiently pure for use in the next step.

Step G: 4-Chloromethyl-1-triphenylmethylimidazole

The product from Step F is dissolved in chloroform and cooled to 0° C. under nitrogen. Thionyl chloride (molar equivalent) is added slowly via syringe. The reaction is stirred for 30 min, and extracted with sodium bicarbonate solution. The organic phase is dried over magnesium sulfate, filtered and concentrated to provide the title compound.

Step H: 4-Diethylphosphonomethyl-1-triphenylmethylimidazole

The product from Step G is dissolved in acetonitrile and cooled to 0° C. Triethyl phosphite (1 equivalent) and sodium iodide (1 equivalent) were added, and the reaction stirred at room temperature overnight. The reaction is quenched with ammonium chloride, and extracted with ethyl acetate. The organic phase is dried over magnesium sulfate, filtered and concentrated to provide the title compound.

Step I: 4-[2-{1-(Triphenylmethyl)-4-imidazolyl}ethenyl]-1-phenyl-2-piperidinone

The product from Step H is dissolved in THF and cooled to −78° C. under nitrogen. A solution of LDA in THF is added dropwise. The reaction is stirred at −78° C. for 1 h, then a solution of 4-formyl-1-phenyl-2-piperidinone from Step E is added, and the reaction warmed to room temperature overnight. The reaction is quenched with ammonium chloride solution, and extracted with ethyl acetate. The title compound is obtained after chromatography on silica gel Step J: 4-[2-{1-(Triphenylmethyl)-4-imidazolyl}ethyl]-1-phenyl-2-piperidinone The product from Step I is dissolved in methanol and hydrogenated at 60 psi hydrogen with 10% palladium on carbon. When reaction is complete, the catalyst is filtered and the title compound obtained after evaporation of solvent.

Step K: 4-[2-{1-(4-Cyanobenzyl)-5-imidazolyl}ethyl]-1-phenyl-2-piperidinone hydrochloride The product from Step J is dissolved in acetonitrile and reacted with 4-cyanobenzylbromide (1 equivalent) at room temperature overnight. The reaction is concentrated in vacuo, and the residue dissolved in methanol. The methanol solution is refluxed for 3 h and then concentrated. The residue is partitioned between ethyl acetate and saturated sodium bicarbonate solution. The organic phase is washed with saturated brine, dried over magnesium sulfate, filtered and concentrated. The title compound is obtained after purification by silica gel chromatography, and conversion to the hydrochloride salt.

Example 4

(±)cis- and (±)trans-4-[2-{1-(4-Cyanobenzyl)-5-imidazolyl}ethyl]-3-methyl-1-phenyl-2-piperidinone hydrochloride

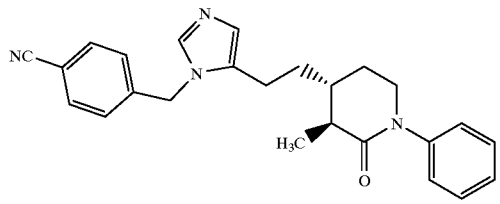

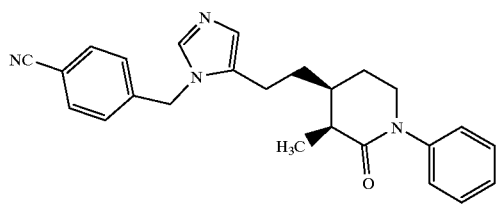

Step A: (±)cis- and (±)trans-3-Methyl-1-phenyl-4-[2-{1-triphenylmethyl)-4-imidazolyl}ethyl]-2-piperidinone 4-[2-{1-(Triphenylmethyl)-4-imidazolyl}ethyl]-1-phenyl-2-piperidinone in THF is added to a solution of 1 eq lithium hexamethyldisilylazide in THF at −78° C., under argon. The reaction is stirred for 30 min, and 1 eq methyl iodide is added. The reaction is warmed to room temperature, quenched with saturated ammonium sulfate solution, and extracted with ethyl acetate. The organic phase is washed with saturated brine and dried over magnesium sulfate. The crude products are purified by columum chromatography and provide the title compounds.

Step B: (±)cis- and (±)trans-4-[2-{1-(4-Cyanobenzyl)-5-imidazolyl}ethyl]-3-methyl-1-phenyl-2-piperidinone hydrochloride The title compound is prepared according to the procedure described in Example 3, Step K, except using the product from Step A in place of 4-[2-{1-(triphenylmethyl)-4-imidazolyl}ethyl]-1-phenyl-2-piperidinone. The title compound is obtained after purification by silica gel chromatography, and conversion to the hydrochloride salt.

Example 5

4-[2-{1-(4-Cyanobenzyl)-5-imidazolyl}carbonyl]-1-phenyl-2-piperidinone hydrochloride

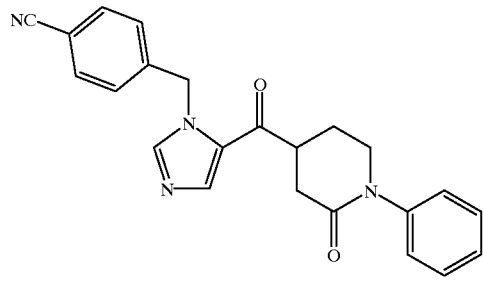

Step A: N-Methyl N-methoxy 1-phenyl-2-piperidinone-4-carboxamide

1-Phenyl-2-piperidinone-4-carboxylic acid is stirred with 1 eq N,O-dimethylhydroxylamine hydrochloride, 1.1 eq EDC·HCl, 1 eq hydroxybenzotriazole in DMF at pH 7 overnight. The reaction is poured into water and extracted with ethyl acetate. The organic phase is dried over magnesium sulfate, filtered and concentrated, and provides the title compound.

Step B: 1-Phenyl-4-[1-triphenylmethyl-4-imidazolyl]carbonyl]-2-piperidinone hydrochloride 1-Triphenylmethylimidazole-4-magnesium iodide in methylene chloride is prepared as described by R. M. Turner, S. D. Lindell and S. V. Ley in J. Org. Chem., 1991, 56, 5739–5740, and is added to 1 eq of N-methyl N-methoxy 1-phenyl-2-piperidinone-4-carboxamide in dichloromethane under argon at −78° C. The reaction is warmed to room temperature and quenched with saturated ammonium chloride solution. The reaction is extracted with ethyl acetate and the organic phase dried over magnesium sulfate, filtered and concentrated, providing the title compound.

Step C: 4-[2-{1-(4-Cyanobenzyl)-5-imidazolyl}carbonyl]-1-phenyl-2-piperidinone hydrochloride The title compound is prepared according to the procedure described in Example 3, Step K, except using the product from Step B in place of 4-[2-{1-(triphenylmethyl)-4-imidazolyl}ethyl]-1-phenyl-2-piperidinone. The title compound is obtained after purification by silica gel chromatography, and conversion to the hydrochloride salt.

Example 6

Preparation of Ethyl 1-[3-(4-cyanobenzyl)-3H-imidazol-4-ylmethyl]-3-oxo-4-(3-methylbenzyl) piperidine-4-carboxylate trifluoroacetate salt

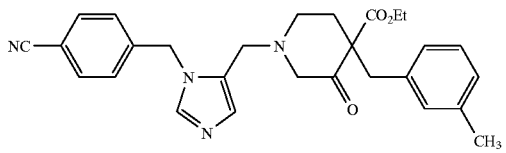

Step A: Preparation of Ethyl N-tert-butoxycarbonyl-3-oxo-piperidine-4-carboxylate A mixture of ethyl N-benzyl-3-oxo-piperidine-4-carboxylate hydrochloride salt (3.5 g, 11.7 mmol; purified) and 10% palladium on charcoal (0.35 g) in a mixture of ethanol (100 mL) and water (100 mL) was hydrogenated at room temp. at 60 psi overnight. The resultant mixture was filtered through a plug of Celite, and the filtrate was concentrated under vacuum. The residue was dissolved in mixture of triethylamine (5 mL), dioxane (20 mL) and water (19 mL), and treated with di-tert-butyl dicarbonate (3.2 g). The reaction mixture was stirred at room temp. overnight. The product mixture was concentrated and the residue was partitioned between ethyl acetate and aqueous sodium bicarbonate. The organic extract was washed with brine, dried over anhydrous magnesium sulfate, filtered, and concentrated under vacuum. The residue was subjected to column chromatography on silica gel eluting with 20% ethyl acetate in hexane. Collection and concentration of appropriate fractions provided the title compound as clear colorless oil, which was stored under argon at −10° C.

Step B: Preparation of Ethyl N-tert-butoxycarbonyl-3-oxo-4-(3-methylbenzyl)piperidine-4-carboxylate To a cold (0° C.) slurry of sodium hydride (0.29 g, 12 mmol) in anhydrous dimethylformamide (50 mL), a solution of ethyl N-tert-butoxycarbonyl-3-oxo-piperidine-4-carboxylate (2.73 g, 10 mmol) in DMF (10 mL) was added. The mixture was stirred at 0° C. for 30 min., and at room temp. for 30 min. The resultant solution was cooled back to 0° C. and treated with 3-methylbenzyl bromide (1.63 mL, 12 mmol). The reaction mixture was stirred at room temp. overnight and concentrated under vacuum. The residue was partitioned between ethyl acetate and aqueous sodium bicarbonate. The organic extract was washed with brine, dried over anhydrous magnesium sulfate, filtered, and concentrated under vacuum. The residue was subjected to column chromatography on silica gel eluting with 17.5% ethyl acetate in hexane. Collection and concentration of appropriate fractions provided the title compound.

Step C: Preparation of Ethyl 3-oxo-4-(3-methylbenzyl)piperidine-4-carboxylate hydrochloride salt To a cold (0° C.) solution of ethyl N-tert-butoxycarbonyl-3-oxo-4-(3-methylbenzyl)piperidine-4-carboxylate (1.55 g, 4.13 mmol) in ethyl acetate (75 mL), a stream of anhydrous hydrogen chloride gas was bubbled for 20 min. The resultant mixture was stirred at 0° C. for 1 h, purged with argon for 10 min., and concentrated under vacuum to provide the title compound as white solid.

Step D: Preparation of Ethyl 1-[3-(4-cyanobenzyl)-3H-imidazol-4-ylmethyl]-3-oxo-4-(3-methylbenzyl)piperidine-4-carboxylate trifluoroacetate salt A solution of ethyl 3-oxo-4-(3-methylbenzyl)piperidine-4-carboxylate hydrochloride salt (4.13 mmol), 1-(4-cyanobenzyl)-5-chloromethylimidazole hydrochloride salt (1.11 g, 4.13 mmol), and diisopropylethylamine (1.58 mL, 9.1 mmol) in anhydrous acetonitrile (10 mL) was heated under reflux overnight. The resultant mixture was concentrated under vacuum, and the residue was partitioned between saturated aqueous sodium bicarbonate and ethyl acetate. The organic extract was washed with brine, dried over anhydrous sodium sulfate, filtered, and concentrated under vacuum. The residue was subjected to column chromatography on silica gel eluting with a 1:1 mixture of chloroform and chloroform saturated with ammonia gas. After collection and concentration of appropriate fractions, the residue further purified by subjecting to high pressure liquid column chromatography on C-18 reverse phase stationary phase. Collection and lyophilization of appropriate fractions provided the title compound as white solid. Anal. Calcd for $C_{28}H_{30}N_4O_3 \cdot 1.6$ TFA·0.1 $H_2O$: C, 57.23; H, 4.90; N, 8.56. Found: C, 57.21; H, 4.85; N, 8.53.

Example 7
In vitro inhibition of ras farnesyl transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM $ZnCl_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples are tested for inhibitory activity against human FPTase by the assay described above. The compound of the instant invention described in Examples 1 and 6 were tested for inhibitory activity against human FPTase by the assay described above and were found to have $IC_{50}$ of $\leq 10$ μM.

Example 8
In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 9
In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula A:

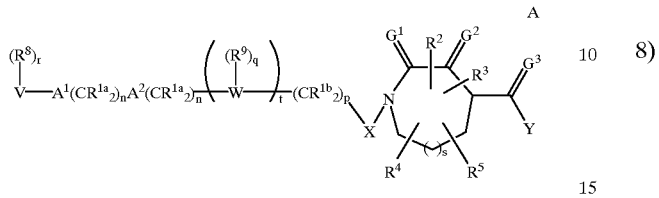

wherein:

$R^{1a}$ and $R^{1b}$ are independently selected from:
  a) hydrogen,
  b) aryl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $N_3$, —$N(R^{10})_2$, or $R^{11}OC(O)NR^{10}$—, and
  c) unsubstituted or substituted $C_1$–$C_6$ alkyl wherein the substitutent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $N_3$, —$N(R^{10})_2$, and $R^{11}OC(O)$—$NR^{10}$—;

$R^2$ and $R^3$ are independently selected from: H; unsubstituted or substituted $C_1$–$C_8$ alkyl, unsubstituted or substituted $C_{2-8}$ alkenyl, unsubstituted or substituted $C_{2-8}$ alkynyl, unsubstituted or substituted aryl, unsubstituted or substituted

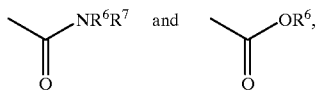

wherein the substituted group is substituted with one or more of:

1) aryl or unsubstituted or substituted with:
  a) $C_{1-4}$ alkyl,
  b) $(CH_2)_pOR^6$,
  c) $(CH_2)_pNR^6R^7$,
  d) halogen,
  e) CN,
  f) aryl,
  g) perfluoro-$C_{1-4}$ alkyl,
  h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$,
5) —$NR^6R^7$,
6) 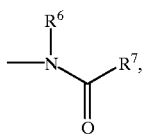

7) 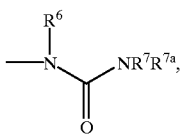

8) 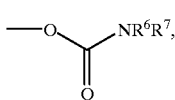

9) 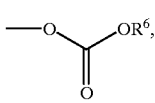

10) 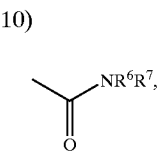

11) —$SO_2$—$NR^6R^7$,

12) 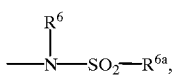

13) 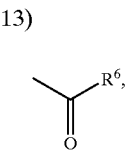

14) 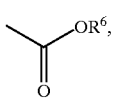

15) $N_3$,
16) F, or
17) perfluoro-$C_{1-4}$-alkyl; or $R^2$ and $R^3$ are attached to the same C atom and are combined to form —$(CH_2)_u$—;

$R^4$ and $R^5$ are independently selected from H and $CH_3$; and any two of $R^2$, $R^3$, $R^4$ and $R^5$ are optionally attached to the same carbon atom;

$R^6$, $R^7$ and $R^{7a}$ are independently selected from: H; $C_{1-4}$ alkyl, $C_{3-6}$ cycloalkyl, aryl, aroyl, and arylsulfonyl, unsubstituted or substituted with:
  a) $C_{1-4}$ alkoxy,
  b) aryl, c) halogen,
d) HO,
e)

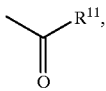

f) —SO$_2$R$^{11}$, or
g) N(R$^{10}$)$_2$; or

R$^{6a}$ is selected from: C$_{1-4}$ alkyl, C$_{3-6}$ cycloalkyl and aryl, unsubstituted or substituted with:
a) C$_{1-4}$ alkoxy,
b) aryl,
c) halogen,
d) HO,
e)

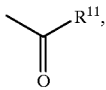

f) —SO$_2$R$^{11}$, or
g) N(R$^{10}$)$_2$;

R$^8$ is independently selected from:
a) hydrogen,
b) aryl, C$_{3-C10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NH—, and
c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$ C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:
a) hydrogen,
b) C$_{2-C6}$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_{1-C6}$ alkyl, benzyl and aryl;
R$^{11}$ is independently selected from C$_{1-C6}$ alkyl and aryl;
A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$— and S(O)$_m$;
G$^1$ and G$^2$ are independently oxygen or absent, provided that at least one of G$^1$ and G$^2$ is oxygen;
G$^3$ is oxygen or H$_2$;
V is selected from:
a) hydrogen,
b) aryl,
c) C$_1$–C$_{20}$ alkyl wherein from 0 to 4 carbon atoms are replaced with a heteroatom selected from O, S, and N, and
d) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is imidazolyl or pyridyl;
X is a bond, —CH$_2$—, —C(=O)—, or —S(=O)$_m$—;
Y is unsubstituted or substituted aryl, wherein the substituted aryl is substituted with one or more of:
1) C$_{1-4}$ alkyl, unsubstituted or substituted with:
  a) C$_{1-4}$ alkoxy,
  b) NR$^6$R$^7$,
  c) C$_{3-6}$ cycloalkyl,
  d) aryl,
  e) HO,
  f) —S(O)$_m$R$^{6a}$, or
  g) —C(O)NR$^6$R$^7$,
2) aryl,
3) halogen,
4) OR$^6$,
5) NR$^6$R$^7$,
6) CN,
7) NO$_2$,
8) CF$_3$;
9) —S(O)$_m$R$^{6a}$,
10) —C(O)NR$^6$R$^7$, or
11) C$_3$–C$_6$ cycloalkyl;
m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0;
t is 0 or 1; and
u is 4 or 5; or an optical isomer or pharmaceutically acceptable salt thereof.

2. A compound which inhibits farnesyl-protein transferase of the formula B:

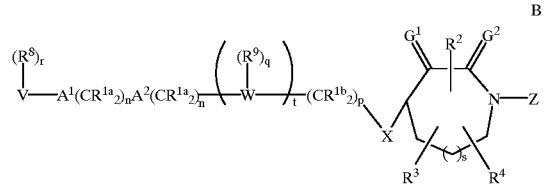

wherein:
R$^{1a}$ and R$^{1b}$ are independently selected from:
a) hydrogen,
b) aryl, C$_3$–C$_{10}$ cycloalkyl, C$_2$–C$_6$ alkenyl, C$_2$–C$_6$ alkynyl, R$^{10}$)—, R$^{11}$S(O)$_m$—, R$^{10}$C(O)NR$^{10}$—, CN(R$^{10}$)$_2$NC(O)—, R$^{10}$$_2$ N—C(NR$^{10}$)—, CN, NO$_2$, R$^{10}$C(O)—, N$_3$, —N(R$^{10}$)$_2$, or R$^{11}$OC(O)—NR$^{10}$—, and
c) unsubstituted or substituted C$_1$–C$_6$ alkyl wherein the substitutent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

R$^2$ and R$^3$ are independently selected from: H; unsubstituted or substituted C$_1$–C$_8$ alkyl, unsubstituted or substituted C$_{2-8}$ alkenyl, unsubstituted or substituted C$_{2-8}$ alkynyl, unsubstituted or substituted aryl, unsubstituted or substituted

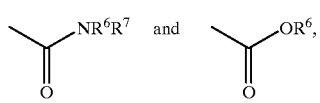 and 

wherein the substituted group is substituted with one or more of:

1) aryl, unsubstituted or substituted with:
   a) $C_{1-4}$ alkyl,
   b) $(CH_2)_p OR^6$,
   c) $(CH_2)_p NR^6R^7$,
   d) halogen,
   e) CN,
   f) aryl,
   g) perfluoro-$C_{1-4}$ alkyl,
   h) $SR^{6a}$, $S(O)R^{6a}$, $S(O)R^{6a}$,
2) $C_{3-6}$ cycloalkyl,
3) $OR^6$,
4) $SR^{6a}$, $S(O)R^{6a}$, or $SO_2R^{6a}$,
5) $-NR^6R^7$,
6) 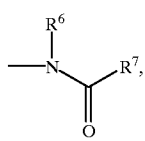
7) 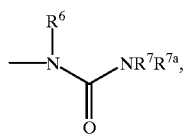
8) 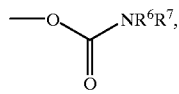
9) 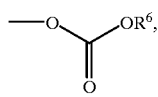
10) 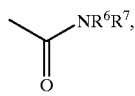
11) $-SO_2-NR^6R^7$,
12) 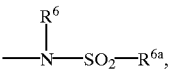
13) 
14) 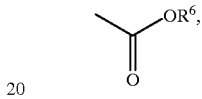
15) $N_3$,
16) F, or
17) perfluoro-$C_{1-4}$-alkyl; or $R^2$ and $R^3$ are attached to the same C atom and are combined to form $-(CH_2)_u-$;

$R^4$ is selected from H and $CH_3$; and any two of $R^2$, $R^3$ and $R^4$ are optionally attached to the same carbon atom;

$R^6$, $R^7$ and $R^{7a}$ are independently selected from: H; $C_{1-4}$ alkyl, $C_{3-6}$ cycloalkyl, aryl, aroyl and arylsulfonyl, unsubstituted or substituted with:
   a) $C_{1-4}$ alkoxy,
   b) aryl,
   c) halogen,
   d) HO,
   e) 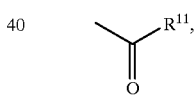
   f) $-SO_2R^{11}$, or
   g) $N(R^{10})_2$; or $R^{6a}$ is selected from: $C_{1-4}$ alkyl, $C_{3-6}$ cycloalkyl and aryl, unsubstituted or substituted with:
   a) $C_{1-4}$ alkoxy,
   b) aryl,
   c) halogen,
   d) HO,
   e) 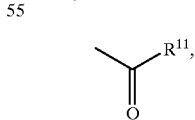
   f) $-SO_2R^{11}$, or
   g) $N(R^{10})_2$;

$R^8$ is independently selected from:
   a) hydrogen,
   b) aryl, $C_3-C_{10}$ cycloalkyl, $C_2-C_6$ alkenyl, $C_2-C_6$ alkynyl, perfluoroalkyl, F, Cl, Br, $R^{10}O-$, $R^{11}S$ (O)$_m$—, R$^{10}$C(O)NR$^{10}$—, (R$^{10}$)$_2$NC(O)—, R$^{10}{}_2$N—C(NR$^{10}$)—, CN, NO$_2$, R$^{10}$C(O)—, N$_3$, —N(R$^{10}$)$_2$, or R$^{11}$OC(O)NR$^{10}$—, and c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}{}_2$N—C(NR$^{10}$)—, CN, R$^{10}$C(O)—, N$_3$, —N(R$^{10}$)$_2$, or R$^{10}$OC(O)NH—;

R$^9$ is selected from:

a) hydrogen, b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, NO$_2$, R$^{10}$C(O)—, N$_3$, —N(R$^{10}$)$_2$, or R$^{11}$OC(O)NR$^{10}$—, and c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$— and S(O)$_m$;

G$^1$ and G$^2$ are independently oxygen or absent provided that at least one of G$^1$ and G2 is oxygen;

V is selected from:

a) hydrogen, b) aryl, c) C$_1$–C$_{20}$ alkyl wherein from 0 to 4 carbon atoms are replaced with a heteroatom selected from O, S, and N, and d) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is imidazolyl or pyridyl;

X is a bond, —CH$_2$—, —C(=O)—, or —S(=O)$_m$—;

Z is selected from:

1) a unsubstituted or substituted group selected from aryl, arylmethyl, and arylsulfonyl, wherein the substituted group is substituted with one or more of the following:
 a) C$_{1-4}$ alkyl, unsubstituted or substituted with:
  C$_{1-4}$ alkoxy, NR$^6$R$^7$, C$_{3-6}$ cycloalkyl, aryl, HO, —S(O)$_m$R$^{6a}$, or —C(O)NR$^6$R$^7$,
 b) aryl,
 c) halogen,
 d) OR$^6$,
 e) NR$^6$R$^7$,
 f) CN,
 g) NO$_2$,
 h) CF$_3$;
 i) —S(O)$_m$R$^{6a}$,
 j) —C(O)NR$^6$R$^7$, or
 k) C$_3$–C$_6$ cycloalkyl; and 2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
 a) C$_{1-4}$ alkoxy,
 b) NR$^6$R$^7$,
 c) C$_{3-6}$ cycloalkyl,
 d) —NR$^6$C(O)R$^7$,
 e) HO,
 f) —S(O)$_m$R$^{6a}$,
 g) halogen, or
 h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0;
t is 0 or 1; and
u is 4 or 5; or a pharmaceutically acceptable salt thereof.

3. A compound which inhibits farnesyl-protein transferase of the formula C:

wherein:

R$^{1a}$ and R$^{1b}$ are independently selected from:

a) hydrogen, b) aryl, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$NC(O)—, R$^{10}{}_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and c) unsubstituted or substituted C$_1$–C$_6$ alkyl wherein the substitutent on the substituted C$_1$–C$_6$ alkyl is selected from unsubstituted or substituted aryl, C$_3$–C$_{10}$ cycloalkyl, C$_2$–C$_6$ alkenyl, C$_2$–C$_6$ alkynyl, R$^{10}$O —, R$^{11}$S(O)$_m$—, R$^{10}$C(O)NR$^{10}$—, (R$^{10}$)$_2$NC(O)—, R$^{10}{}_2$N—C(NR$^{10}$)—, CN, R$^{10}$C(O)—, R$^{10}$OC(O)—, N$_3$, —N(R$^{10}$)$_2$, and R$^{11}$OC(O)—NR$^{10}$—;

R$^2$ and R$^3$ are independently selected from: H; unsubstituted or substituted C$_1$–C$_8$ alkyl, unsubstituted or substituted C$_{2-8}$ alkenyl, unsubstituted or substituted C$_{2-8}$ alkynyl, unsubstituted or substituted aryl, unsubstituted or substituted wherein the substituted group is substituted with one or more of:

1) aryl, unsubstituted or substituted with:
 a) C$_{1-4}$ alkyl,
 b) (CH$_2$)$_p$OR$^6$,
 c) (CH$_2$)$_p$NR$^6$R$^7$,
 d) halogen,
 e) CN,
 f) aryl,
 g) perfluoro-C$_{1-4}$ alkyl,
 h) SR$^{6a}$, S(O)R$^{6a}$, SO$_2$R$^{6a}$, 2) C$_{3-6}$ cycloalkyl,
3) OR$^6$,
4) SR$^{6a}$, S(O)R$^{6a}$, or SO$_2$R$^{6a}$,
5) —NR$^6$R$^7$, 6) 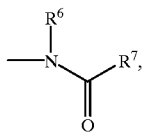

7) 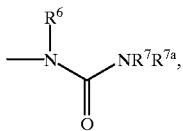

8) 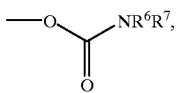

9) 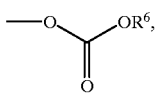

10) 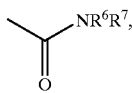

11) —SO$_2$—NR$^6$R$^7$,

12) 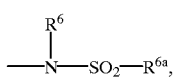

13) 

14) 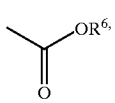

15) N$_3$,

16) F, or 17) perfluoro-C$_{1-4}$-alkyl; or

R$^2$ and R$^3$ are attached to the same C atom and are combined to form —(CH$_2$)$_u$—;

R$^4$ is selected from H and CH$_3$; and any two of R$^2$, R$^3$ and R$^4$ are optionally attached to the same carbon atom;

R$^6$, R$^7$ and R$^{7a}$ are independently selected from: H; C$_{1-4}$ alkyl, C$_{3-6}$ cycloalkyl, aryl, aroyl and arylsulfonyl, unsubstituted or substituted with:

a) C$_{1-4}$ alkoxy,
b) aryl,
c) halogen,
d) HO,
e) 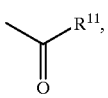

f) —SO$_2$R$^{11}$, or
g) N(R$^{10}$)$_2$; or

R$^{6a}$ is selected from: C$_{1-4}$ alkyl, C$_{3-6}$ cycloalkyl and aryl, unsubstituted or substituted with:

a) C$_{1-4}$ alkoxy,
b) aryl,
c) halogen,
d) HO,
e) 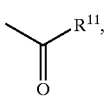

f) —SO$_2$R$^{11}$, or
g) N(R$^{10}$)$_2$;

R$^8$ is independently selected from:

a) hydrogen,
b) aryl, C$_3$–C$_{10}$ cycloalkyl, C$_2$–C$_6$ alkenyl, C$_2$–C$_6$ alkynyl, perfluoroalkyl, F, Cl, Br, R$^{10}$O —, R$^{11}$S (O)$_m$—, R$^{10}$C(O)NR$^{10}$—, (R$^{10}$)$_2$NC(O)—, R$^{10}$$_2$N—C (NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O —, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:

a) hydrogen,
b) C$_2$–C$_6$ alkenyl, C$_2$–C$_6$ alkynyl, perfluoroalkyl, F, Cl, Br, R$^{10}$O —, R$^{11}$S(O)$_m$—, R$^{10}$C(O)NR$^{10}$—, (R$^{10}$)$_2$NC (O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O —, R$^{11}$S(O)$_m$—, R$^{10}$C (O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR10—;

R$^{10}$ is independently selected from hydrogen, C$_1$–C$_6$ alkyl, benzyl and aryl;

R$_{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$— and S(O)$_m$;

G$^1$ and G$^2$ are independently oxygen or absent, provided that if G$^1$ is oxygen then G$^2$ is absent and if s=0, G$^1$ is oxygen;

V is selected from:
 a) hydrogen,
 b) aryl,
 c) C$_1$–C$_{20}$ alkyl wherein from 0 to 4 carbon atoms are replaced with a heteroatom selected from O, S, and N, and
 d) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is imidazolyl or pyridyl;

X is a bond, —CH$_2$—, —C(=O)—, or —S(=O)$_m$—;

Z is selected from:
 1) a unsubstituted or substituted group selected from aryl, arylmethyl, and arylsulfonyl, wherein the substituted group is substituted with one or more of the following:
   a) C$_{1-4}$ alkyl, unsubstituted or substituted with:
     C$_{1-4}$ alkoxy, NR$^6$R$^7$, C$_{3-6}$ cycloalkyl, aryl, HO, —S(O)$_m$R$^{6a}$, or —C(O)NR$^6$R$^7$,
   b) aryl,
   c) halogen,
   d) OR$^6$,
   e) NR$^6$R$^7$,
   f) CN,
   g) NO$_2$,
   h) CF$_3$;
   i) —S(O)$_m$R$^{6a}$,
   j) —C(O)NR$^6$R$^7$, or
   k) C$_3$–C$_6$ cycloalkyl; and
 2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
   a) C$_{1-4}$ alkoxy,
   b) NR$^6$R$^7$,
   c) C$_{3-6}$ cycloalkyl,
   d) —NR$^6$C(O)R$^7$,
   e) HO,
   f) —S(O)$_m$R$^{6a}$,
   g) halogen, or
   h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0;
t is 0 or 1; and
u is 4 or 5; or a pharmaceutically acceptable salt thereof.

4. The compound according to claim 2 of the formula B:

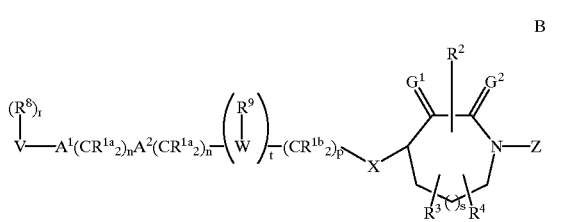

wherein:
R$^{1a}$ is independently selected from: hydrogen and C$_1$–C$_6$ alkyl;

R$^{1b}$ is independently selected from:
 a) hydrogen,
 b) aryl, cycloalkyl, R$^{10}$O —, —N(R$^{10}$)$_2$ or C$_2$–C$_6$ alkenyl, and
 c) unsubstituted or substituted C$_1$–C$_6$ alkyl wherein the substitutent on the substituted C$_1$–C$_6$ alkyl is selected from unsubstituted or substituted aryl, cycloalkyl, alkenyl, R$^{10}$O — and —N(R$^{10}$)$_2$;

R$^3$ and R$^4$ are independently selected from H and CH$_3$;

R$^2$ is H;

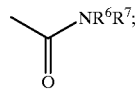

or C$_{1-5}$ alkyl, unbranched or branched, unsubstituted or substituted with one or more of:
 1) aryl,
 2) OR$^6$,
 3) SR$^{6a}$, SO$_2$R$^{6a}$, or
 4)

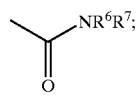

and any two of R$^2$, R$^3$, and R$^4$ are optionally attached to the same carbon atom;

R$^6$, R$^7$ and R$^{7a}$ are independently selected from:
 H; C$_{1-4}$ alkyl, C$_{3-6}$ cycloalkyl, and aryl, unsubstituted or substituted with:
  a) C$_{1-4}$ alkoxy,
  b) halogen, or
  c) aryl;

R$^6$a is selected from:
 C$_{1-4}$ alkyl and C$_{3-6}$ cycloalkyl, unsubstituted or substituted with:
  a) C$_{1-4}$ alkoxy,
  b) halogen, or
  c) aryl;

R$^8$ is independently selected from:
 a) hydrogen,
 b) C$_1$–C$_6$ alkyl, C$_2$–C$_6$ alkenyl, C$_2$–C$_6$ alkynyl, Cl–C$_6$ perfluoroalkyl, F, Cl, R$^{10}$O —, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^9$ is selected from:
 a) hydrogen,
 b) C$_2$–C$_6$ alkenyl, C$_2$–C$_6$ alkynyl, C$_1$–C$_6$ perfluoroalkyl, F, Cl, R$^{10}$O —, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl unsubstituted or substituted by C$_1$–C$_6$ perfluoroalkyl, F, Cl, R$^{10}$O —, R$^{11}$S(O)$_m$—, R$^{10}$C(O)NR$^{10}$—, CN, (R$^{10}$)$_2$N—C(NR$^{10}$)—, R$^{10}$C(O)—, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

$A^1$ and $A^2$ are independently selected from: a bond, —CH=CH—, —C≡C—, —C(O)—, —C(O)NR$^{10}$—, O, —N(R$^{10}$)— and S(O)$_m$;

V is selected from:
a) hydrogen,
b) aryl,
c) $C_1$–$C_{20}$ alkyl wherein from 0 to 4 carbon atoms are replaced with a heteroatom selected from O, S, and N, and
d) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

$G^1$ is absent;
$G^2$ is oxygen;
W is imidazolyl or pyridyl;
X is —CH$_2$— or —C(=O)—;
Z is selected from:
1) a unsubstituted or substituted group selected from aryl, arylmethyl, and arylsulfonyl, wherein the substituted group is substituted with one or more of the following:
   a) $C_{1-4}$ alkyl, unsubstituted or substituted with:
      $C_{1-4}$ alkoxy, NR$^6$R$^7$, $C_{3-6}$ cycloalkyl, aryl, HO, —S(O)$_m$R$^{6a}$, or —C(O)NR$^6$R$^7$,
   b) aryl,
   c) halogen,
   d) OR$^6$,
   e) NR$^6$R$^7$,
   f) CN,
   g) NO$_2$,
   h) CF$_3$;
   i) —S(O)$_m$R$^{6a}$,
   j) —C(O)NR$^6$R$^7$, or
   k) $C_3$–$C_6$ cycloalkyl; and
2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
   a) $C_{1-4}$ alkoxy,
   b) NR$^6$R$^7$,
   c) $C_{3-6}$ cycloalkyl,
   d) —NR$^6$C(O)R$^7$,
   e) HO,
   f) —S(O)$_m$R$^{6a}$,
   g) halogen, or
   h) perfluoroalkyl;

m is 0, 1 or 2;
n is 0, 1, 2, 3 or 4;
p is 0, 1, 2, 3 or 4;
r is 0 to 5, provided that r is 0 when V is hydrogen;
s is 0;
t is 0 or 1; and
u is 4 or 5; or a pharmaceutically acceptable salt thereof.

5. The compound according to claim 2 of the formula D:

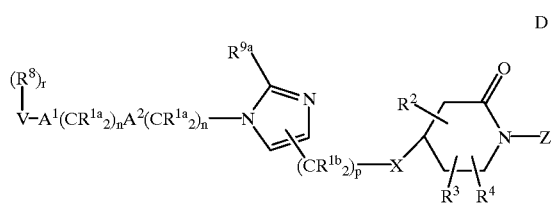

wherein:
R$^{1a}$ is selected from: hydrogen and $C_1$–$C_6$ alkyl;

R$^{1b}$ is independently selected from:
a) hydrogen,
b) aryl, cycloalkyl, R$^{10}$O —, —N(R$^{10}$)$_2$ or $C_2$–$C_6$ alkenyl, and
c) $C_1$–$C_6$ alkyl unsubstituted or substituted by aryl, cycloalkyl, alkenyl, R$^{10}$O—, or —N(R$^{10}$)$_2$;

R$^3$ and R$^4$ independently selected from H and CH$_3$;
R$^2$ is selected from H;

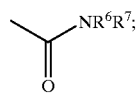

and $C_{1-5}$ alkyl, unbranched or branched, unsubstituted or substituted with one or more of:
1) aryl,
2) OR$^6$,
3) SR$^{6a}$, SO$_2$R$^{6a}$, or
5)

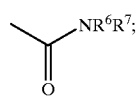

and R$^2$, R$^3$ and R$^4$ are optionally attached to the same carbon atom;

R$^6$ and R$^7$ are independently selected from:
H; $C_{1-4}$ alkyl, $C_{3-6}$ cycloalkyl, and aryl, unsubstituted or substituted with:
   a) $C_{1-4}$ alkoxy,
   b) halogen, or
   c) aryl;

R$^{6a}$ is selected from:
$C_{1-4}$ alkyl and $C_{3-6}$ cycloalkyl, unsubstituted or substituted with:
   a) $C_{1-4}$ alkoxy,
   b) halogen, or
   c) aryl;

R$^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, R$^{10}$O —, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$_{11}$OC(O)NR$^{10}$—, and
c) $C_1$–$C_6$ alkyl substituted by $C_1$–$C_6$ perfluoroalkyl, R$^{10}$O —, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;
R$^{10}$ is independently selected from hydrogen, $C_1$–$C_6$ alkyl, benzyl and aryl;
R$^{11}$ is independently selected from $C_1$–$C_6$ alkyl and aryl;
$A^1$ and $A^2$ are independently selected from: a bond, —CH=CH—, —C≡C—, —C(O)—, —C(O)NR$^{10}$—, O, —N(R$^{10}$)— and S(O)$_m$;

V is selected from:
a) hydrogen,
b) aryl,
c) $C_1$–$C_{20}$ alkyl wherein from 0 to 4 carbon atoms are replaced with a heteroatom selected from O, S, and N, and
d) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

X is —CH$_2$— or —C(=O)—;
Z is selected from:
1) a unsubstituted or substituted group selected from aryl, arylmethyl, and arylsulfonyl, wherein the substituted group is substituted with one or more of the following:
   a) C$_{1-4}$ alkyl, unsubstituted or substituted with:
      C$_{1-4}$ alkoxy, NR$^6$R$^7$, C$_{3-6}$ cycloalkyl, aryl, HO, —S(O)$_m$R$^{6a}$, or —C(O)NR$^6$R$^7$,
   b) aryl,
   c) halogen,
   d) OR$^6$,
   e) NR$^6$R$^7$,
   f) CN,
   g) NO$_2$,
   h) CF$_3$;
   i) —S(O)$_m$R$^{6a}$,
   j) —C(O)NR$^6$R$^7$, or
   k) C$_3$–C$_6$ cycloalkyl; and
2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
   a) C$_{1-4}$ alkoxy,
   b) NR$^6$R$^7$,
   c) C$_{3-6}$ cycloalkyl,
   d) —NR$^6$C(O)R$^7$,
   e) HO,
   f) —S(O)$_m$R$^{6a}$,
   g) halogen, or
   h) perfluoroalkyl;
m is 0, 1 or 2;
n is 0, 1, 2, 3 or 4;
p is 0, 1, 2, 3 or 4; and
r is 0 to 5, provided that r is 0 when V is hydrogen; or a pharmaceutically acceptable salt thereof.

6. The compound according to claim 2 of the formula E:

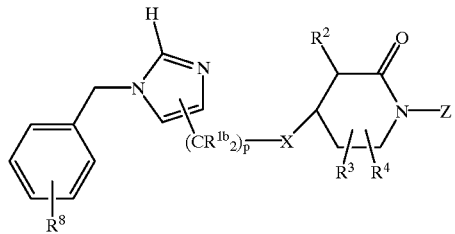

E wherein:
R$^{1b}$ is independently selected from:
   a) hydrogen,
   b) aryl, cycloalkyl, R$^{10}$O—, —N(R$^{10}$)$_2$ or C$_2$–C$_6$ alkenyl, and
   c) C$_1$–C$_6$ alkyl unsubstituted or substituted by aryl, cycloalkyl, alkenyl, R$^{10}$O—, or —N(R$^{10}$)$_2$;
R$^3$ and R$^4$ independently selected from H and CH$_3$;
R$^2$ is selected from H;

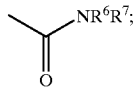

and C$_{1-5}$ alkyl, unbranched or branched, unsubstituted or substituted with one or more of:
   1) aryl,
   2) OR$^6$,
   3) SR$_{6a}$, SO$_2$R$^{6a}$, or
   4)

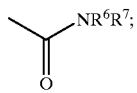

and R$^2$, R$^3$ and R$^4$ are optionally attached to the same carbon atom;
R$^6$ and R$^7$ are independently selected from:
   H; C$_{1-4}$ alkyl, C$_{3-6}$ cycloalkyl, and aryl, unsubstituted or substituted with:
      a) C$_{1-4}$ alkoxy,
      b) halogen, or
      c) aryl;
R$^{6a}$ is selected from:
   C$_{1-4}$ alkyl and C$_{3-6}$ cycloalkyl, unsubstituted or substituted with:
      a) C$_{1-4}$ alkoxy,
      b) halogen, or
      c) aryl;
R$^8$ is independently selected from:
   a) hydrogen,
   b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{10}$C(O)NR$^{10}$—, and
   c) C$_1$–C$_6$ alkyl substituted by C$_1$–C$_6$ perfluoroalkyl, R$^{10}$$_0$—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;
R$^{10}$ is independently selected from hydrogen, C$_1$–C$_6$ alkyl, benzyl and aryl;
R$^{11}$ is independently selected from C$_1$–C$_6$ alkyl and aryl;
X is —CH$_2$— or —C(=O)—;
Z is selected from:
1) a unsubstituted or substituted group selected from aryl, arylmethyl, and arylsulfonyl, wherein the substituted group is substituted with one or more of the following:
   a) C$_{1-4}$ alkyl, unsubstituted or substituted with:
      C$_{1-4}$ alkoxy, NR$^6$R$^7$, C$_{3-6}$ cycloalkyl, aryl, HO, —S(O)$_m$R$^{6a}$, or —C(O)NR$^6$R$^7$,
   b) aryl,
   c) halogen,
   d) OR$^6$,
   e) NR$^6$R$^7$,
   f) CN,
   g) NO$_2$,
   h) CF$_3$;
   i) —S(O)$_m$R$^{6a}$,
   j) —C(O)NR$^6$R$^7$, or
   k) C$_3$–C$_6$ cycloalkyl; and
2) unsubstituted C$_1$–C$_6$ alkyl, substituted Cl–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
   a) C$_{1-4}$ alkoxy,
   b) NR$^6$R$^7$,
   c) C$_{3-6}$ cycloalkyl,
   d) —NR$^6$C(O)R$^7$,
   e) HO,
   f) —S(O)$_m$R$^{6a}$, g) halogen, or
h) perfluoroalkyl;

m is 0, 1 or 2; and p is 0, 1, 2, 3 or 4; or a pharmaceutically acceptable salt thereof.

7. The compound according to claim 2 of the formula F:

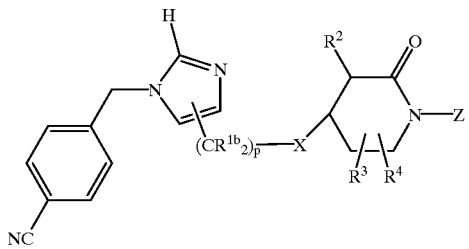

wherein:

$R^{1b}$ is independently selected from:
a) hydrogen,
b) aryl, cycloalkyl, $R^{10}O—$, $—N(R^{10})_2$ or $C_2$–$C_6$ alkenyl, and
c) $C_1$–$C_6$ alkyl unsubstituted or substituted by aryl, cycloalkyl, alkenyl, $R^{10}O—$, or $—N(R^{10})_2$;

$R^3$ and $R^4$ independently selected from H and $CH_3$;
$R^2$ is selected from H;

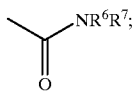

and $C_{1-5}$ alkyl, unbranched or branched, unsubstituted or substituted with one or more of:
1) aryl,
2) $OR^6$,
3) $SR^{6a}$, $SO_2R^{6a}$, or
4)

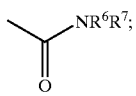

and $R^2$, $R^3$ and $R^4$ are optionally attached to the same carbon atom;

$R^6$ and $R^7$ are independently selected from:
H; $C_{1-4}$ alkyl, $C_{3-6}$ cycloalkyl, and aryl, unsubstituted or substituted with:
a) $C_{1-4}$ alkoxy,
b) halogen, or
c) aryl;

$R^{6a}$ is selected from:
$C_{1-4}$ alkyl and $C_{3-6}$ cycloalkyl, unsubstituted or substituted with:
a) $C_{1-4}$ alkoxy,
b) halogen, or
c) aryl;

$R^{10}$ is independently selected from hydrogen, $C_1$–$C_6$ alkyl, benzyl and aryl;

$R^{11}$ is independently selected from $C_1$–$C_6$ alkyl and aryl;

X is $—CH_2—$ or $—C(=O)—$;

Z is selected from:
1) a unsubstituted or substituted group selected from aryl, arylmethyl, and arylsulfonyl, wherein the substituted group is substituted with one or more of the following:

a) $C_{1-4}$ alkyl, unsubstituted or substituted with:
$C_{1-4}$ alkoxy, $NR^6R^7$, $C_{3-6}$ cycloalkyl, aryl, HO, $—S(O)_mR^{6a}$, or $—C(O)NR^6R^7$,
b) aryl,
c) halogen,
d) $OR^6$,
e) $NR^6R^7$,
f) CN,
g) $NO_2$,
h) $CF_3$;
i) $—S(O)_mR^{6a}$,
j) $—C(O)NR^6R^7$, or
k) $C_3$–$C_6$ cycloalkyl; and 2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
a) $C_{1-4}$ alkoxy,
b) $NR^6R^7$,
c) $C_{3-6}$ cycloalkyl,
d) $—NR^6C(O)R^7$,
e) HO,
f) $—S(O)_mR^{6a}$,
g) halogen, or
h) perfluoroalkyl;

m is 0, 1 or 2; and p is 0, 1, 2, 3 or 4; or pharmaceutically acceptable salt thereof.

8. A compound which inhibits farnesyl-protein transferase which is:

4-[5-(4-Cyanobenzyl)imidazol-1-ylmethyl]-1-phenyl-2-piperidinone

4-[2-{5-(4-Cyanobenzyl)imidazol-1-yl}ethyl]-1-phenyl-2-piperidinone

4-[2-{1-(4-Cyanobenzyl)-5-imidazolyl}ethyl]-1-phenyl-2-piperidinone (±)cis-4-[2-{1-(4-Cyanobenzyl)-5-imidazolyl}ethyl]-3-methyl-1-phenyl-2-piperidinone (±)trans-4-[2-{1-(4-Cyanobenzyl)-5-imidazolyl}ethyl]-3-methyl-1-phenyl-2-piperidinone 4-[2-{1-(4-Cyanobenzyl)-5-imidazolyl}carbonyl]-1-phenyl-2-piperidinone or Ethyl 1-[3-(4-cyanobenzyl)-3H-imidazol-4-ylmethyl]-3-oxo-4-(3-methylbenzyl)piperidine-4-carboxylate or a pharmaceutically acceptable salt or optical isomer thereof.

9. The compound according to claim 8 which is:

4-[5-(4-Cyanobenzyl)imidazol-1-ylmethyl]-1-phenyl-2-piperidinone

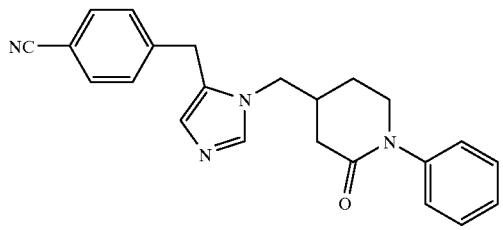

or a pharmaceutically acceptable salt or optical isomer thereof.

10. The compound according to claim 8 which is:

4-[2-{5-(4-Cyanobenzyl)imidazol-1-yl}ethyl]-1-phenyl-2-piperidinone

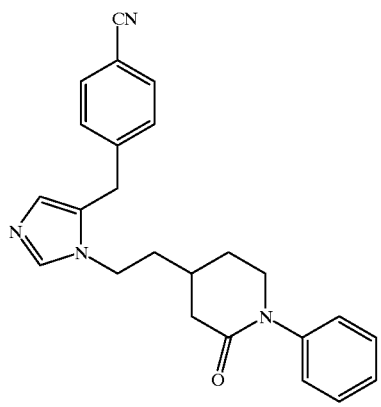

or a pharmaceutically acceptable salt or optical isomer thereof.

11. A pharmaceutical composition comprising a pharmaceutical carrier, and dispersed therein, a therapeutically effective amount of a compound of claim 1.

12. A pharmaceutical composition comprising a pharmaceutical carrier, and dispersed therein, a therapeutically effective amount of a compound of claim 2.

13. A pharmaceutical composition comprising a pharmaceutical carrier, and dispersed therein, a therapeutically effective amount of a compound of claim 3.

14. A pharmaceutical composition comprising a pharmaceutical carrier, and dispersed therein, a therapeutically effective amount of a compound of claim 8.

15. A method for inhibiting farnesyl-protein transferase which comprises administering to a mammal in need thereof a therapeutically effective amount of a composition of claim 11.

16. A method for inhibiting farnesyl-protein transferase which comprises administering to a mammal in need thereof a therapeutically effective amount of a composition of claim 12.

17. A method for inhibiting farnesyl-protein transferase which comprises administering to a mammal in need thereof a therapeutically effective amount of a composition of claim 13.

18. A method for inhibiting farnesyl-protein transferase which comprises administering to a mammal in need thereof a therapeutically effective amount of a composition of claim 14.

19. A pharmaceutical composition made by combining the compound of claim 2 and a pharmaceutically acceptable carrier.

20. A process for making a pharmaceutical composition comprising combining a compound of claim 2 and a pharmaceutically acceptable carrier.

* * * * *

UNITED STATES PATENT AND TRADEMARK OFFICE
CERTIFICATE OF CORRECTION

PATENT NO. : 5,965,578
DATED : October 12, 1999
INVENTOR(S) : Samuel L. Graham, et. al.

It is certified that error appears in the above-identified patent and that said Letters Patent is hereby corrected as shown below:

In Claim 1, column 59, line 30 should read as follows:
-- b) aryl, $C_3$-$C_{10}$ cycloalkyl, $C_2$-$C_6$ alkenyl, $C_2$-$C_6$ alkynyl, -- .

In Claim 1, column 59, line 33 should read as follows:
-- $NO_2$, $R^{10}C(O)$-, $N_3$, -$N(R^{10})_2$, or $R^{11}OC(O)NR^{10}$-, -- .

In Claim 1, column 59, line 43 should read as follows:
-- b) $C_2$-$C_6$ alkenyl, $C_2$-$C_6$ alkynyl, perfluoroalkyl, F, Cl, Br, -- .

In Claim 1, column 59, line 51 should read as follows:
-- $R^{10}$ is independently selected from hydrogen, $C_1$-$C_6$ alkyl, -- .

In Claim 1, column 59, line 53 should read as follows:
-- $R^{11}$ is independently selected from $C_1$-$C_6$ alkyl and aryl; -- .

In Claim 2, column 60, line 52 should read as follows:
-- alkynyl, $R^{10}O$-, $R^{11}S(O)_m$-, $R^{10}C(O)NR^{10}$-, -- .

In Claim 2, column 61, line 20 should read as follows:
-- h) $SR^{6a}$, $S(O)R^{6a}$, $S(O)_2R^{6a}$, -- .

In Claim 2, column 63, line 25 should read as follows:
-- -CH=CH-, -C≡C-, -C(O)-, -C(O)$NR^{10}$-, -- .

In Claim 2, column 63, line 29 should read as follows:
-- at least one of $G^1$ and $G^2$ is oxygen; -- .

UNITED STATES PATENT AND TRADEMARK OFFICE
CERTIFICATE OF CORRECTION

PATENT NO. : 5,965,578
DATED : October 12, 1999
INVENTOR(S) : Samuel L. Graham, et. al.

It is certified that error appears in the above-identified patent and that said Letters Patent is hereby corrected as shown below:

In Claim 3, column 66, line 67 should read as follows:
-- $-CH=CH-, -C{\equiv}C-, -C(O)-, -C(O)NR^{10}-,$ -- .

In Claim 4, column 68, line 47 should read as follows:
-- b) $C_1$-$C_6$ alkyl, $C_2$-$C_6$ alkenyl, $C_2$-$C_6$ alkynyl, $C_1$-$C_6$ -- .

In Claim 6, column 72, line 33 should read as follows:
-- $R^{10}O-, R^{10}C(O)NR^{10}-, (R^{10})_2N-C(NR^{10})-, R^{10}C$ -- .

Signed and Sealed this

Second Day of May, 2000

Q. TODD DICKINSON

Attest:

Attesting Officer

Director of Patents and Trademarks